US007041288B2

(12) United States Patent
Kricek et al.

(10) Patent No.: US 7,041,288 B2
(45) Date of Patent: May 9, 2006

(54) ANTI-IDIOTYPIC ANTIBODIES AGAINST ANTIBODIES WHICH INHIBIT THE BINDING OF IMMUNOGLOBULIN E TO ITS HIGH AFFINITY RECEPTORS

(75) Inventors: Franz Kricek, Biedermannsdorf (AT); Beda Stadler, Bern (CH); Monique Vogel, Bern (CH)

(73) Assignee: Novartis AG, Basel (CH)

( * ) Notice: Subject to any disclaimer, the term of this patent is extended or adjusted under 35 U.S.C. 154(b) by 99 days.

(21) Appl. No.: 09/974,449

(22) Filed: Oct. 10, 2001

(65) Prior Publication Data

US 2002/0141989 A1 Oct. 3, 2002

Related U.S. Application Data

(63) Continuation of application No. PCT/EP00/03288, filed on Apr. 12, 2000.

(30) Foreign Application Priority Data

Apr. 14, 1999 (GB) .................................... 9908533

(51) Int. Cl.
*A61K 39/395* (2006.01)
*C07K 16/42* (2006.01)
(52) U.S. Cl. ................................ 424/131.1; 530/387.2
(58) Field of Classification Search ............. 424/131.1; 530/387.2
See application file for complete search history.

(56) References Cited

U.S. PATENT DOCUMENTS 4,816,567 A 3/1989 Cabilly et al.

FOREIGN PATENT DOCUMENTS

| EP | 0 141 783 | | 10/1984 |
|---|---|---|---|
| EP | 0 731 167 A1 | | 7/1988 |
| EP | 0 449 112 A1 | | 2/1992 |
| JP | 11000174 A | | 1/1999 |
| WO | WO 89/06138 | | 7/1989 |
| WO | WO 91/11456 | | 8/1991 |
| WO | WO 94/07922 | | 4/1994 |
| WO | WO 95/07933 | | 3/1995 |
| WO | WO 97/31948 | * | 9/1997 |
| WO | WO 99/01556 | | 1/1999 |
| WO | WO 99/55911 | | 11/1999 |

OTHER PUBLICATIONS

Mikayama et al. (PNAS, 1993., 90: 10056-10060).*
Ngo et al.; The Protein Folding Problem and Tertiary Structure Prediction, 1994, Merz et al., (ed.), Birkhauser, Boston, MA, pp. 433 and 492-495.*
Cruise et al. (Illustrated Dictionary of Immunology, CRC Press, New York, 1995, pp. 18-20 and 107-109).*
Jerne et al. ( The EMBO J. 1982; 1(2): 243-245).*
Sambrook et al. (Molecular Cloning: A Laboratory Manual; 1989. 2nd ed. Cold Spring Harbor Laboratory Press, New York. p. 17.2).*
Kuby et al., 1994, Immunology, second edition, pp. 85-96.*
Abaza et al, J of Protein Chemistry 11(5): 433-444, 1992.*
Boutin et al.,., "Manipulation of the Idiotypic Network. An Alternative Approach to Treat Allergic Asthma?", Immunotherapy in Asthma, ed. Bousquet et al., vol. 136, pp. 337-349, Marcel Dekker, Inc.: New York (1999).
Boutin et al., "Modulation of Immune Response to Loi p 1 by Pretreatment with Anti-Idiotypic Antibody Is Not Restricted to the Idiotypic Expression", Clin. Exp. Immunol., vol. 96, pp. 350-355 (1994).
Boutin et al., "Biological Activity of Monoclonal Anti-Idiotypic Antibody Representing the Internal Image of the Major Allergenic Component of Lolium Perenne Pollen", Int. Arch. Allergy Immunol., vol. 102, pp. 10-14 (1993)—[94004033 MEDLINE].
Baniyash et al., "Anti-Anti-IgE Idiotypic Antibodies Minic IgE in Their Binding to the $Fc_\epsilon$Receptor", Eur. J. Immunol., vol. 17, pp. 1337-1342 (1987).
Bowman et al., "The Complete Nucleotide Sequence of Chromosome3 of Plasmodium Falciparum", Nature, vol. 400, No. 6744, pp. (1999)—[1999:516759 HCAPLUS].

(Continued)

*Primary Examiner*—Christina Chan
*Assistant Examiner*—Phuong Huynh
(74) *Attorney, Agent, or Firm*—Gregory C. Houghton

(57) ABSTRACT

Antibodies and antibody fragments which are anti-idiotypic to an antibody that interferes with the binding of the $C\epsilon 3$ region of IgE to its high affinity receptor (mimobodies), particularly, which are anti-idiotypic to BSW17 (BSW17-mimobodies) are described, as well as their use as pharmaceuticals, especially vaccines, in the treatment of IgE-mediated diseases.

4 Claims, 20 Drawing Sheets

OTHER PUBLICATIONS

Czech et al., "IgE Autoantibodies in Atopic Dermatitis—Occurrence of Different Antibodies Against CH3 and the CH4 Epitopes of IgE", Allergy, vol. 50, pp. 243-248 (1995).

Hirano et al., "Studies on Murine IgE with Monoclonal Antibodies", Int. Archs. Allergy Appl. Immun., vol. 85, pp. 47-54 (1988).

Ito et al., "Cloning and Nucleotide Sequence Determination of the Entire Mec DNA of Pre-Methicillin-Resistant *Staphylococcus Aureus* N315", Antimicrob. Agents Chemother., vol. 43, No. 6, pp. (1999)—[1999:369433 HCAPLUS].

Mockridge et al., "Sequence Analysis of V4-34-Encoded Antibodies from Single B Cells of Two Patients with Systemic Lupus Erythematosus (SLE)", Clin. Exp. Immunol., vol. 114, No. 1, pp. (1998)—[1998:698755 HCAPLUS].

Kricek et al., "IgE-Related Peptide Mimotopes", Int. Arch. Allergy Immunol., vol. 118, pp. 222-223 (1999).

Nakajima et al., "Effect of Anti-IgE Antibodies on IgE Binding to CD23", Allergy, vol. 44, No. 3, pp. 187-191 (1989)—[1989:240665 BIOSIS].

Rudolf et al., "Epitope-Specific Antibody Response to IgE by Mimotope Immunization", J. Immunol., vol. 160, No. 7, pp. 3315-3321 (1998).

Saint-Remy "Suppression de la Réponse Immunitaire IgE àl'Aide d'Anticorps Spécifiques", Rev. Fr. Allergol., vol. 34, No. 5, pp. 94)—[19943473037 EMBASE].

Rudolf et al., "Effect of Anti-IgE Antibodies on FcεRI-Bound IgE", J. Immunol., vol. 157, pp. 5646-5652 (1996).

Shanti et al, "Identification of Tropomyosin as the Major Shrimp Allergen and Characterization of Its IgE-Binding Epitopes", J. Immunol., vol. 151, No. 10, pp. 5354-5363 (1993).

Ravirajan et al., "Genetic, Structural, and Functional Properties of An IgG DNA-Binding Monoclonal Antibody from a Lupus Patient with Nephritis", Eur. J. Immunol., vol. 28, No. 1, pp. (1998)—[1998:98832 HCAPLUS].

Spiegelberg et al., "Lack of Pokeweed Mitogen-Induced IgE Formation In Vitro by Human Peripheral Blood Mononuclear Cells: Detection of Cross-Reacting Idiotypic Determinants on Polyclonal Ig by Antibodies to a Single IgE Myeloma Protein", J. Immunol., vol. 131, No. 6, pp. 3001-3005 (1983).

Stadler et al., "Can Active Immunization Redirect an Anti-IgE Immune Response?", Int. Arch. Allergy Immunol., vol. 113, pp. 216-218 (1997).

Stadler et al., "Anti-IgE Vaccination", Prog. Allergy Clin. Immunol., vol. 4, pp. 339-342 (1997)

Stadler et al., "Regulation of Immunoglobulin E Inflammation Anti-Immunoglulin E Autoantibodies", Immunotherapy in Asthma, ed. Bousquet et al., vol. 136, pp. 431-438, Marcell Dekker, Inc.: New York (1999).

Stadler et al., "Mimotope and Anti-Idiotypic Vaccines to Induce an Anti-IgE Response", Int. Arch. Allergy Immunol., vol. 118, pp. 119-121 (1999), From Molecular Science to the Treatment of Allergy, 22$^{nd}$ Symposium of the Collegium Internationale Allergologicum, eds. Togias et al., Corfu, Greece, 1998).

Sun et al, "Gene Structure, Chromosomal Localizatrion, and Expression of the Murine Homolog of Human Proteinase Inhibitor 6 (Pl-6) Suggest Divergence of Pl-6 from the Ovalbumin Serpins", J. Biol. Chem., vol. 270, No. 27, pp. (1995)—[1995:685421 HCAPLUS].

Vogel et al., "Human Anti-IgE Antibodies by Repertoire Cloning", Eur. J. Immunol., vol. 24, pp. 1200-1207 (1994).

Vogel et al., "Role of Anti-Idiotypic Antibodies in IgE Regulation", The XXVth Anniversary Meeting of the International Soiciety for Oncodevelopmental Biology and Medicine, Montreux, Switzerland (Sep. 19-24, 1997), From Basic Cancer Research to Clinical Application, vol. 18, ,Supp. 2, p. 59 (1997).

Chang, "The Pharmacological Basis of Anti-IgE Therapy", Nature Biotechnology, vol. 18, pp. 157-162 (2000).

Zuercher et al., "Oral Anti-IgE Immunization with Epitope-Displaying Phage", Eur. J. Immunol., vol. 30, pp. 128-135 (2000).

Yu et al., "Anti-IgE Autoantibodies and Bee-Sting Allergy", Allergy, vol. 50, No. 2, pp. (1995)—[1995:293059 BIOSIS].

* cited by examiner

ANTI-BSW17 FAB CLONE 52: VARIABLE HEAVY CHAIN: DNA SEQUENCE OF BACTERIOPHAGE-DISPLAYED HUMAN IMMUNOGLOBULIN AND DEDUCED AMINO ACID SEQUENCE. HYPERVARIABLE REGIONS (COMPLEMENTARITY DETERMINING REGIONS; CDR) ARE SHOWN IN ITALICS

```
                    9                              18              27                      36                  45                          54
5' CAG  GTG  AAA  CTG  CTC  GAG  TCC  GGG  GGA  GGC  CTG  GTC  AAG  CCT  GGG  GGG  TCC  CTG
   Q    V    K    L    L    E    S    G    G    G    L    V    K    P    G    G    S    L 63                             72              81                      90                  99                          108
   AGA  CTC  TCC  TGT  GCA  GCC  TCT  GGA  TTC  ACC  TTC  AGT  AAC  TAT  AAT  ATG  AAC  TGG
   R    L    S    C    A    A    S    G    F    T    F    S    N    Y    N    M    N    W
                                                                        CDR1

117                            126             135                     144                 153                         162
   GTC  CGC  CAG  GCT  CCA  GGG  AAG  GGA  CTA  GAG  TGG  GTG  GTC  TCA  TCC  ATT  AGT  AGT  CGA
   V    R    Q    A    P    G    K    G    L    E    W    V    V    S    S    I    S    S    R
                                                                             CDR2

171                            180             189                     198                 207                         216
   AAT  TCT  TAC  ATA  TAC  TAC  GCA  GAC  TCA  GTG  AAG  GGC  CGA  TTC  ACC  ATC  TCC  AGA
   N    S    Y    I    Y    Y    A    D    S    V    K    G    R    F    T    I    S    R 225                            234             243                     252                 261                         270
   GAC  AAC  GCC  GCT  AGT  ACC  TTG  TAT  CTG  CAA  ATG  GAC  ATG  CTG  GGA  ATG  GAA  GAC
   D    N    A    A    S    T    L    Y    L    Q    M    D    M    L    G    V    E    D
                                                                    CDR3

279                            288             306                     315                 324
   ACG  GCT  GTC  TGT  TGT  GCC  AGC  GGC  CGC  CTT  TTC  GAC  TAC  TGG  GGC  CAG  GGA
   T    A    V    C    C    A    S    G    R    L    F    D    Y    W    G    Q    G
            CDR3

333                            342
   ACC  CTG  GTC  ACC  GTC  TCC  TCT  3'
   T    L    V    T    V    S    S
```

FIG. 5A

ANTI-BSW17 FAB CLONE 52: VARIABLE LIGHT CHAIN: DNA SEQUENCE OF BACTERIOPHAGE-DISPLAYED HUMAN IMMUNOGLOBULIN AND DEDUCED AMINO ACID SEQUENCE. HYPERVARIABLE REGIONS (COMPLEMENTARITY DETERMINING REGIONS; CDR) ARE SHOWN IN ITALICS

```
5'  GTG ATG ACC CAG TCT CCA TCC TCA TCT GCA GTA GAC AGA GTC ACC
     V   M   T   Q   S   P   S   S   S   A   V   D   R   V   T
                 9              18              27              36              45              54

ATC ACT TGT CGG GCT AGT CAG AGT ATT AAC AAC TAT TTA GCC TGG TTT CAG CAG
     I   T   C   R   A   S   Q   S   I   N   N   Y   L   A   W   F   Q   Q
                63  CDR1            72              81              90              99              108

AAA CCA GGG AAA GCC CCT AAG CTC ATC TAT TAT GCA TCC ATT TTG CAA AGT
     K   P   G   K   A   P   K   L   I   Y   Y   A   S   I   L   Q   S
                117             126             135    CDR2   144             153             162

GGG GTC CCA TCA AGG TTC AGC GGA GGA TAT GAT ACA TCC ACT CTC ACC
     G   V   P   S   R   F   S   G   G   Y   D   T   S   T   L   T
                171             180             189             198             207             216

ATC AGC AAC CTG CAG CCT GAA GAT TTT GCA ACT TAT TAC TGC CAA CAA TAT AAT
     I   S   N   L   Q   P   E   D   F   A   T   Y   Y   C   Q   Q   Y   N
                225             234             243             252          CDR3  261             270

TAT TAT CCG CTC ACT TTC GGC GGA GGG ACC AAG GTG GAG ATC AAA
     Y   Y   P   L   T   F   G   G   G   T   K   V   E   I   K   3'
                279             288             297             306             315
```

FIG. 5B

ANTI-BSW17 FAB CLONE 43: VARIABLE LIGHT CHAIN: DNA SEQUENCE OF BACTERIOPHAGE-DISPLAYED HUMAN IMMUNOGLOBULIN AND DEDUCED AMINO ACID SEQUENCE. HYPERVARIABLE REGIONS (COMPLEMENTARITY DETERMINING REGIONS; CDR) ARE SHOWN IN ITALICS

```
5'                9                 18                27                36                45                54
   CAG GTG CTG   AAA CTG CTC   GAG TCG GGC   CCA GGA CTG   GTG AAG CCT   TCG GAG ACC   CTG
    Q   V   L     K   L   L     E   S   G     P   G   L     V   K   P     S   E   T     L
                 63                72                81       CDR1     99               108
   TCC CTC       ACC TGC ACT   GTC TCT GGT   GGC TCC ATC   AGC AGT GGT   GGT TAC TGG
    S   L         T   C   T     V   S   G     G   S   I     S   S   G     G   Y   W
                 117              126               135               144               162
   ACC TGG       ATC CGC CAG   CCA CCA GGG   AAG GGC CTG   GAG TGG ATT   GGA TAC TAT
    T   W         I   R   Q     P   P   G     K   G   L     E   W   I     G   Y   Y
                                              CDR2
                 171              180               189               198               216
   TAC AGT       GGG AGC ACC   TCC TAC AAC   CCC TCC CTC   AAG AGT CGA   GTC ATC TCA
    Y   S         G   S   T     S   Y   N     P   S   L     K   S   R     V   I   S
                 225              234               243               252               270
   GTG GAC       ACG TCT AAA   AAC CAG TTC   TCC CTG AGG   CTG ACC TCT   GTG ACT GCC GGG
    V   D         T   S   K     N   Q   F     S   L   R     L   T   S     V   T   A
                                                              CDR3
                 279              288               297               306               324
   GAC GCC       GCC GTC TAT   TAC TGT GCG   CGA GAG CGG   GGT GAG ACC   CTA TAT TAC
    D   A         A   V   Y     Y   C   A     R   E   R     G   E   T     L   Y   Y
                 333              342               351               360               378
   CCC TAT       TAC TAC ATA   GAC GTC TGG   GGC ACA GGG   ACC ACC GTC   TCC TCA
    P   Y         Y   Y   I     D   V   W     G   T   G     T   T   V     S   S      3'
```

FIG. 5C

ANTI-BSW17 FAB CLONE 43: VARIABLE LIGHT CHAIN: DNA SEQUENCE OF BACTERIOPHAGE-DISPLAYED HUMAN IMMUNOGLOBULIN AND DEDUCED AMINO ACID SEQUENCE. HYPERVARIABLE REGIONS (COMPLEMENTARITY DETERMINING REGIONS; CDR) ARE SHOWN IN ITALICS

```
5'
      9                    18            27                   36            45            54
GAG   GTC   GTG   ACT   CAG   CCT   GCC   TCC   GTG   TCT   GGG   TCT   CCT   GGA   CAG   ATC
 E     L     V     T     Q     P     A     S     V     S     G     S     P     G     Q     I 63                   72            81                                  99           108
ACC   ATC   TGC   ACT   GGA   ACC   AGA   AGT   GAC   GTT   GGT   GGT   TAT   AAC   TCG   TCC
 T     I     C     T     G     T     R     S     D     V     G     G     Y     N     S     S
             CDR1

117                  126           135                  144           153           162
TGG   TAC   CAA   CAA   CAC   CCA   GGC   AAA   CCC   CCC   AAA   CTC   ATG   ATT   TAT   GAT   GTC   AGT
 W     Y     Q     Q     H     P     G     K     P     P     K     L     M     I     Y     D     V     S
                                                                                        CDR2

171                  180           189                  198           207           216
AAT   CGG   TCA   GGG   GTT   TCT   AAT   CGC   TTC   TCT   GGC   TCC   AAG   TCT   GGC   ACG
 N     R     S     G     V     S     N     R     F     S     G     S     K     S     G     T 225                  234           243                  252           261           270
GCC   TCC   ACC   ATC   TCT   GGG   CTC   CAG   GCT   GAG   GAC   GAG   GCT   GAT   TAT   TAC   TGC
 A     S     T     I     S     G     L     Q     A     E     D     E     A     D     Y     Y     C

CDR3
     279                  288           297                  306           315           324
AGC   TAT   ACA   AGC   AGC   ACT   CTC   GGG   TTC   GAG   GGA   GGG   ACC   AAG   TTG
 S     Y     T     S     S     T     L     G     F     E     G     G     T     K     L 333                  342
ACC   GTC   CTA   GGT   CAG   CCC
 T     V     L     G     Q     P     3'
```

FIG.5D

AMINO ACID SEQUENCE HOMOLOGY BETWEEN ANTI-BSW17 rFAB AND THE Cε3 DOMAIN OF HUMAN IgE

ANTI-ID FAB, CLONE 52; HEAVY CHAIN:

```
      370            379       383
    V N L T W S R - A S G

AMINO ACID SEQUENCE HOMOLOGY BETWEEN ANTI-BSW17 rFAB AND THE Cε3 DOMAIN OF HUMAN IgE

ANTI-ID FAB, CLONE 43; HEAVY CHAIN:

```
     355                                              383
     T T C L V V D L A P S

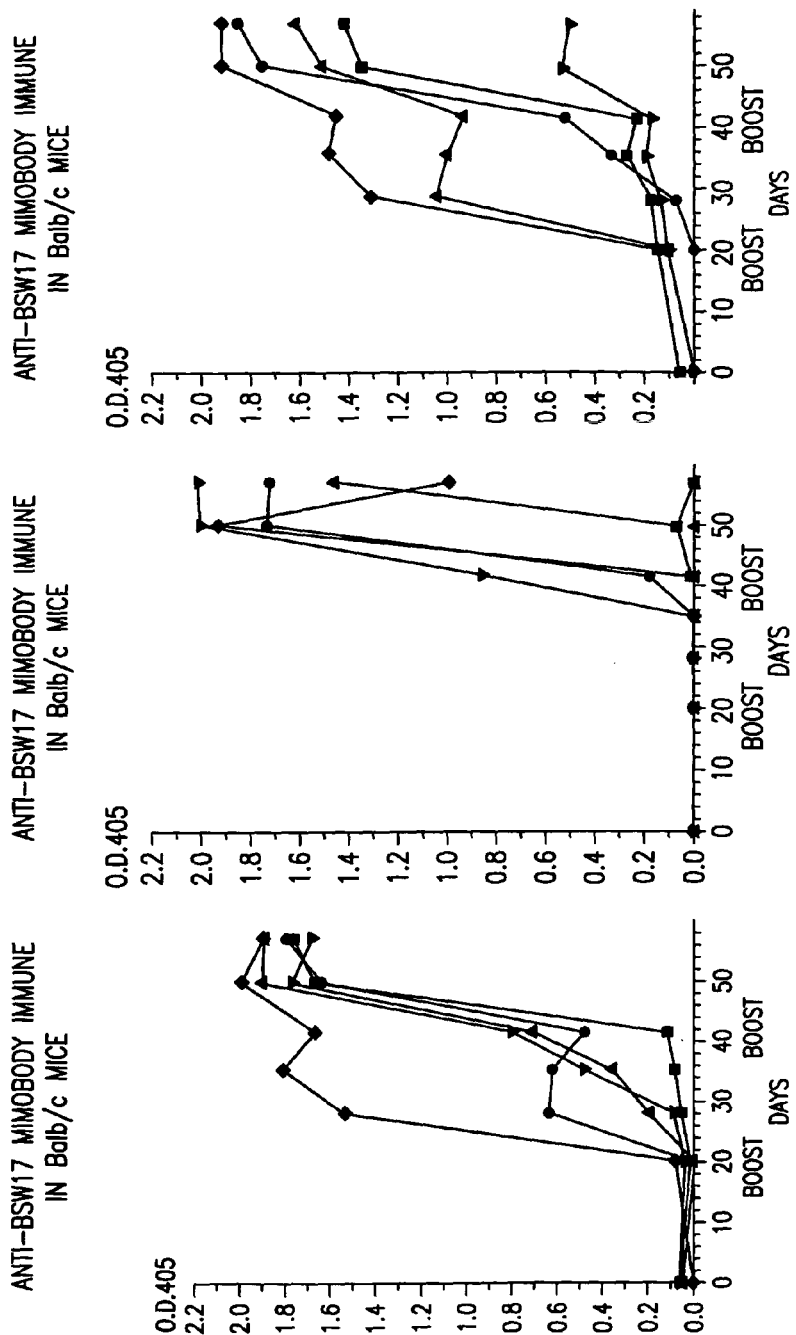

ANTI-BSW17 CLONE 52: VARIABLE AND FIRST CONSTANT DOMAIN OF HEAVY CHAIN

ANTI-BSW17 FAB CLONE 52: VARIABLE AND CONSTANT DOMAIN OF KAPPA LIGHT CHAIN

ANTI-BSW17 FAB CLONE 43: VARIABLE AND FIRST CONSTANT DOMAIN OF HEAVY CHAIN

ANTI-BSW17 FAB CLONE 43: VARIABLE AND FIRST DOMAIN OF LAMBDA LIGHT CHAIN

SEQUENCE LISTING

<160> NUMBER OF SEQ ID NOS: 62

<210> SEQ ID NO 1
<211> LENGTH: 345
<212> TYPE: DNA
<213> ORGANISM: Homo sapiens

<400> SEQUENCE: 1

```
caggtgaaac tgctcgagtc ggggggaggc ctggtcaagc ctggggggtc cctgagactc    60
tcctgtgcag tctctggatt caccttcagt aactataata tgaactgggt ccgccaggct   120
ccagggaagg gactagagtg ggtctcatcc attagtagtc gaaattctta catatactac   180
gcagactcag tgaagggccg attcaccatc tccagagaca acgccgagag taccttgtat   240
ctgcaaatgg acaacctggg agtcgaagac acggctgtct attttgtac gagcggccgc    300
cttttcgact actggggcca gggaaccctg gtcaccgtct cctct                   345
```

<210> SEQ ID NO 2
<211> LENGTH: 115
<212> TYPE: PRT
<213> ORGANISM: Homo sapiens

<400> SEQUENCE: 2

```
Gln Val Lys Leu Leu Glu Ser Gly Gly Gly Leu Val Lys Pro Gly Gly
 1               5                  10                  15
Ser Leu Arg Leu Ser Cys Ala Val Ser Gly Phe Thr Phe Ser Asn Tyr
            20                  25                  30
Asn Met Asn Trp Val Arg Gln Ala Pro Gly Lys Gly Leu Glu Trp Val
        35                  40                  45
Ser Ser Ile Ser Ser Arg Asn Ser Tyr Ile Tyr Tyr Ala Asp Ser Val
    50                  55                  60
Lys Gly Arg Phe Thr Ile Ser Arg Asp Asn Ala Glu Ser Thr Leu Tyr
65                  70                  75                  80
Leu Gln Met Asp Asn Leu Gly Val Glu Asp Thr Ala Val Tyr Phe Cys
                85                  90                  95
Thr Ser Gly Arg Leu Phe Asp Tyr Trp Gly Gln Gly Thr Leu Val Thr
            100                 105                 110
Val Ser Ser
        115
```

<210> SEQ ID NO 3
<211> LENGTH: 315
<212> TYPE: DNA
<213> ORGANISM: Homo sapiens

<400> SEQUENCE: 3

```
gtgatgaccc agtctccatc ctcactgtct gcatctgtag gagacagagt caccatcact    60
tgtcgggcta gtcagggcat taacaattat ttagcctggt ttcagcagaa accagggaaa   120
gcccctaagt ccctgatcta tagtgcatcc attttgcaaa gtggggtccc atccaagttc   180
agcggcagtg gatctgggac agatttcact ctcaccatca gcaacctgca gcctgaagat   240
tttgcaactt attactgcca acaatataat tattatccgc tcactttcgg cggagggacc   300
aaggtggaga tcaaa                                                     315
```

<210> SEQ ID NO 4
<211> LENGTH: 105

```
<212> TYPE: PRT
<213> ORGANISM: Homo sapiens

<400> SEQUENCE: 4

Val Met Thr Gln Ser Pro Ser Ser Leu Ser Ala Ser Val Gly Asp Arg
 1               5                  10                  15

Val Thr Ile Thr Cys Arg Ala Ser Gln Gly Ile Asn Asn Tyr Leu Ala
            20                  25                  30

Trp Phe Gln Gln Lys Pro Gly Lys Ala Pro Lys Ser Leu Ile Tyr Ser
        35                  40                  45

Ala Ser Ile Leu Gln Ser Gly Val Pro Ser Lys Phe Ser Gly Ser Gly
    50                  55                  60

Ser Gly Thr Asp Phe Thr Leu Thr Ile Ser Asn Leu Gln Pro Glu Asp
65                  70                  75                  80

Phe Ala Thr Tyr Tyr Cys Gln Gln Tyr Asn Tyr Tyr Pro Leu Thr Phe
                85                  90                  95

Gly Gly Gly Thr Lys Val Glu Ile Lys
            100                 105

<210> SEQ ID NO 5
<211> LENGTH: 378
<212> TYPE: DNA
<213> ORGANISM: Homo sapiens

<400> SEQUENCE: 5
caggtgaaac tgctcgagtc gggcccagga ctggtgaagc cttcggagac cctgtccctc      60
acctgcactg tctctggtgg ctccatcagc agtggtggtt actactggac ctggatccgc     120
cagcgcccag ggaagggcct ggagtggatt ggatacatct attacagtgg gagcaccctc     180
tacaacccgt ccctcaagag tcgagtcacc atgtcagtgg acacgtctaa aaaccagttc     240
tccctgaggc tgacctctgt gactgccgcg gacacggccg tctattactg tgcgcgagag     300
cggggtgaga ccggtctata ttaccccctat tactacatag acgtctgggg cacagggacc     360
accgtcaccg tctcctca                                                   378

<210> SEQ ID NO 6
<211> LENGTH: 126
<212> TYPE: PRT
<213> ORGANISM: Homo sapiens

<400> SEQUENCE: 6

Gln Val Lys Leu Leu Glu Ser Gly Pro Gly Leu Val Lys Pro Ser Glu
 1               5                  10                  15

Thr Leu Ser Leu Thr Cys Thr Val Ser Gly Gly Ser Ile Ser Ser Gly
            20                  25                  30

Gly Tyr Tyr Trp Thr Trp Ile Arg Gln Arg Pro Gly Lys Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Val Thr Met Ser Val Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Glu Arg Gly Glu Thr Gly Leu Tyr Tyr Pro Tyr Tyr Tyr
                100                 105                 110

Ile Asp Val Trp Gly Thr Gly Thr Thr Val Thr Val Ser Ser
            115                 120                 125
```

<210> SEQ ID NO 7
<211> LENGTH: 342
<212> TYPE: DNA
<213> ORGANISM: Homo sapiens

<400> SEQUENCE: 7

```
gagctcgtgg tgactcagcc tgcctccgtg tctgggtctc ctggacagtc gatcaccatc      60
tcctgcactg gaaccagaag tgacgttggt ggttataact atgtctcctg gtaccaacaa     120
cacccaggca agcccccaa actcatgatt tatgatgtca gtaatcggcc ctcagggggtt     180
tctaatcgct ctctggctc caagtctggc aacacggcct ccctgaccat ctctgggctc     240
caggctgagg acgaggctga ttattactgc agctcatata caagcagcag cactctcggg     300
gtgttcggcg gagggaccaa gttgaccgtc ctaggtcagc cc                        342
```

<210> SEQ ID NO 8
<211> LENGTH: 114
<212> TYPE: PRT
<213> ORGANISM: Homo sapiens

<400> SEQUENCE: 8

Glu Leu Val Val Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Gly Val Phe Gly Gly Gly Thr Lys Leu Thr Val Leu Gly
            100                 105                 110

Gln Pro

<210> SEQ ID NO 9
<211> LENGTH: 29
<212> TYPE: DNA
<213> ORGANISM: Homo sapiens

<400> SEQUENCE: 9

```
cactcccagg tgcagctgct cgagtctgg                                        29
```

<210> SEQ ID NO 10
<211> LENGTH: 32
<212> TYPE: DNA
<213> ORGANISM: Homo sapiens

<400> SEQUENCE: 10

```
gtcctgtccc aggtcaactt actcgagtct gg                                    32
```

<210> SEQ ID NO 11
<211> LENGTH: 32
<212> TYPE: DNA
<213> ORGANISM: Homo sapiens

<400> SEQUENCE: 11

```
gtccaggtgg aggtgcagct gctcgagtct gg                                    32

<210> SEQ ID NO 12
<211> LENGTH: 32
<212> TYPE: DNA
<213> ORGANISM: Homo sapiens

<400> SEQUENCE: 12
gtcctgtccc aggtgcagct gctcgagtcg gg                                    32

<210> SEQ ID NO 13
<211> LENGTH: 32
<212> TYPE: DNA
<213> ORGANISM: Homo sapiens

<400> SEQUENCE: 13
gtctgtgccg aggtgcagct gctcgagtct gg                                    32

<210> SEQ ID NO 14
<211> LENGTH: 32
<212> TYPE: DNA
<213> ORGANISM: Homo sapiens

<400> SEQUENCE: 14
gtcctgtcac aggtacagct gctcgagtca gg                                    32

<210> SEQ ID NO 15
<211> LENGTH: 27
<212> TYPE: DNA
<213> ORGANISM: Homo sapiens

<400> SEQUENCE: 15
agcatcacta gtacaagatt tgggctc                                          27

<210> SEQ ID NO 16
<211> LENGTH: 35
<212> TYPE: DNA
<213> ORGANISM: Homo sapiens

<400> SEQUENCE: 16
gtgccagatg tgagctcgtg atgacccagt ctcca                                 35

<210> SEQ ID NO 17
<211> LENGTH: 56
<212> TYPE: DNA
<213> ORGANISM: Homo sapiens

<400> SEQUENCE: 17
tccttctaga ttactaacac tctcccctgt tgaagctctt tgtgacgggc gaactc          56

<210> SEQ ID NO 18
<211> LENGTH: 36
<212> TYPE: DNA
<213> ORGANISM: Homo sapiens

<400> SEQUENCE: 18
ctgcacaggg tcctgggccg agctcgtggt gactca                                36

<210> SEQ ID NO 19
<211> LENGTH: 34
<212> TYPE: DNA
<213> ORGANISM: Homo sapiens
```

-continued

<400> SEQUENCE: 19
gcattctaga ctattatgaa cattctgtag gggc                    34

<210> SEQ ID NO 20
<211> LENGTH: 18
<212> TYPE: DNA
<213> ORGANISM: Homo sapiens

<400> SEQUENCE: 20
cgctgtgccc ccagaggt                                       18

<210> SEQ ID NO 21
<211> LENGTH: 22
<212> TYPE: DNA
<213> ORGANISM: Homo sapiens

<400> SEQUENCE: 21
ggccgcaaat tctatttcaa gg                                  22

<210> SEQ ID NO 22
<211> LENGTH: 18
<212> TYPE: DNA
<213> ORGANISM: Homo sapiens

<400> SEQUENCE: 22
gagacacacc agtgtggc                                       18

<210> SEQ ID NO 23
<211> LENGTH: 18
<212> TYPE: DNA
<213> ORGANISM: Homo sapiens

<400> SEQUENCE: 23
cacaacagag gcagttcc                                       18

<210> SEQ ID NO 24
<211> LENGTH: 18
<212> TYPE: DNA
<213> ORGANISM: Homo sapiens

<400> SEQUENCE: 24
ctaaactagc tagtcgcc                                       18

<210> SEQ ID NO 25
<211> LENGTH: 14
<212> TYPE: PRT
<213> ORGANISM: Homo sapiens

<400> SEQUENCE: 25

Val Asn Leu Thr Trp Ser Arg Ala Ser Gly Lys Pro Val Asn
 1               5                  10

<210> SEQ ID NO 26
<211> LENGTH: 15
<212> TYPE: PRT
<213> ORGANISM: Homo sapiens

<400> SEQUENCE: 26

Tyr Asn Met Asn Trp Val Arg Gln Ala Pro Gly Lys Gly Leu Glu
 1               5                  10                  15

<210> SEQ ID NO 27
<211> LENGTH: 16

<212> TYPE: PRT
<213> ORGANISM: Homo sapiens

<400> SEQUENCE: 27

Pro Ser Pro Phe Asp Leu Phe Ile Arg Lys Ser Pro Thr Ile Thr Cys
1               5                   10                  15

<210> SEQ ID NO 28
<211> LENGTH: 16
<212> TYPE: PRT
<213> ORGANISM: Homo sapiens

<400> SEQUENCE: 28

Pro Ser Ser Leu Ser Ala Ser Val Gly Asp Arg Val Thr Ile Thr Cys
1               5                   10                  15

<210> SEQ ID NO 29
<211> LENGTH: 10
<212> TYPE: PRT
<213> ORGANISM: Homo sapiens

<400> SEQUENCE: 29

Val Asn Leu Thr Trp Ser Arg Ala Ser Gly
1               5                   10

<210> SEQ ID NO 30
<211> LENGTH: 10
<212> TYPE: PRT
<213> ORGANISM: Homo sapiens

<400> SEQUENCE: 30

Val Thr Ile Thr Cys Arg Ala Ser Gln Gly
1               5                   10

<210> SEQ ID NO 31
<211> LENGTH: 29
<212> TYPE: PRT
<213> ORGANISM: Homo sapiens

<400> SEQUENCE: 31

Thr Ile Thr Cys Leu Val Val Asp Leu Ala Pro Ser Lys Gly Thr Val
1               5                   10                  15

Asn Leu Thr Trp Ser Arg Ala Ser Gly Lys Pro Val Asn
            20                  25

<210> SEQ ID NO 32
<211> LENGTH: 30
<212> TYPE: PRT
<213> ORGANISM: Homo sapiens

<400> SEQUENCE: 32

Ser Leu Thr Cys Thr Val Ser Gly Gly Ser Ile Ser Ser Gly Gly Tyr
1               5                   10                  15

Tyr Trp Thr Trp Ile Arg Gln Arg Pro Gly Lys Gly Leu Glu
            20                  25                  30

<210> SEQ ID NO 33
<211> LENGTH: 25
<212> TYPE: PRT
<213> ORGANISM: Homo sapiens

<400> SEQUENCE: 33

Gly Thr Arg Asp Trp Ile Glu Gly Glu Thr Tyr Gln Cys Arg Val Thr
1               5                   10                  15

-continued

His Pro His Leu Pro Arg Ala Leu Met
         20              25

<210> SEQ ID NO 34
<211> LENGTH: 26
<212> TYPE: PRT
<213> ORGANISM: Homo sapiens

<400> SEQUENCE: 34

Gly Thr Arg Ser Asp Val Gly Gly Tyr Asn Tyr Val Ser Trp Tyr Gln
1               5                   10                  15

Gln His Pro Gly Lys Ala Pro Lys Leu Met
            20                  25

<210> SEQ ID NO 35
<211> LENGTH: 218
<212> TYPE: PRT
<213> ORGANISM: Homo sapiens

<400> SEQUENCE: 35

Gln Val Lys Leu Leu Glu Ser Gly Gly Gly Leu Val Lys Pro Gly Gly
1               5                   10                  15

Ser Leu Arg Leu Ser Cys Ala Val Ser Gly Phe Thr Phe Ser Asn Tyr
            20                  25                  30

Asn Met Asn Trp Val Arg Gln Ala Pro Gly Lys Gly Leu Glu Trp Val
        35                  40                  45

Ser Ser Ile Ser Ser Arg Asn Ser Tyr Ile Tyr Tyr Ala Asp Ser Val
    50                  55                  60

Lys Gly Arg Phe Thr Ile Ser Arg Asp Asn Ala Glu Ser Thr Leu Tyr
65                  70                  75                  80

Leu Gln Met Asp Asn Leu Gly Val Glu Asp Thr Ala Val Tyr Phe Cys
                85                  90                  95

Thr Ser Gly Arg Leu Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Ala Glu Pro Lys Ser Cys
    210                 215

<210> SEQ ID NO 36
<211> LENGTH: 211
<212> TYPE: PRT
<213> ORGANISM: Homo sapiens

<400> SEQUENCE: 36

Val Met Thr Gln Ser Pro Ser Ser Leu Ser Ala Ser Val Gly Asp Arg
1               5                   10                  15

```
Val Thr Ile Thr Cys Arg Ala Ser Gln Gly Ile Asn Asn Tyr Leu Ala
            20                  25                  30

Trp Phe Gln Gln Lys Pro Gly Lys Ala Pro Lys Ser Leu Ile Tyr Ser
        35                  40                  45

Ala Ser Ile Leu Gln Ser Gly Val Pro Ser Lys Phe Ser Gly Ser Gly
 50                  55                  60

Ser Gly Thr Asp Phe Thr Leu Thr Ile Ser Asn Leu Gln Pro Glu Asp
 65                  70                  75                  80

Phe Ala Thr Tyr Tyr Cys Gln Gln Tyr Asn Tyr Tyr Pro Leu Thr Phe
                85                  90                  95

Gly Gly Gly Thr Lys Val Glu Ile Lys Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ile Phe Asn Arg
        195                 200                 205

Gly Glu Cys
        210

<210> SEQ ID NO 37
<211> LENGTH: 229
<212> TYPE: PRT
<213> ORGANISM: Homo sapiens

<400> SEQUENCE: 37

Gln Val Lys Leu Leu Glu Ser Gly Pro Gly Leu Val Lys Pro Ser Glu
 1               5                  10                  15

Thr Leu Ser Leu Thr Cys Thr Val Ser Gly Gly Ser Ile Ser Ser Gly
            20                  25                  30

Gly Tyr Tyr Thr Trp Trp Ile Arg Gln Arg Pro Gly Lys Gly Leu Glu
        35                  40                  45

Trp Ile Gly Tyr Ile Tyr Tyr Ser Gly Ser Thr Ser Tyr Asn Pro Ser
 50                  55                  60

Leu Lys Ser Arg Val Thr Met Ser Val Asp Thr Ser Lys Asn Gln Phe
 65                  70                  75                  80

Ser Leu Arg Leu Thr Ser Val Thr Ala Ala Asp Thr Ala Val Tyr Tyr
                85                  90                  95

Cys Ala Arg Glu Arg Gly Glu Thr Gly Leu Tyr Tyr Pro Tyr Tyr Tyr
            100                 105                 110

Ile Asp Val Trp Gly Thr Gly Thr Thr Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Ala
        210                 215                 220

Glu Pro Lys Ser Cys
225

<210> SEQ ID NO 38
<211> LENGTH: 219
<212> TYPE: PRT
<213> ORGANISM: Homo sapiens

<400> SEQUENCE: 38

Glu Leu Val Val Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Gly Val Phe Gly Gly Gly Thr Lys Leu Thr Val Leu Gly
            100                 105                 110

Gln Pro Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Lys Ser Tyr Ser Cys Gln Val Thr His Glu Gly Ser Thr
        195                 200                 205

Val Glu Lys Thr Val Ala Pro Thr Glu Cys Ser
        210                 215

<210> SEQ ID NO 39
<211> LENGTH: 15
<212> TYPE: DNA
<213> ORGANISM: Homo sapiens

<400> SEQUENCE: 39
aactataata tgaac                                                    15

<210> SEQ ID NO 40
<211> LENGTH: 5
<212> TYPE: PRT
<213> ORGANISM: Homo sapiens

```
<400> SEQUENCE: 40

Asn Tyr Asn Met Asn
 1               5

<210> SEQ ID NO 41
<211> LENGTH: 51
<212> TYPE: DNA
<213> ORGANISM: Homo sapiens

<400> SEQUENCE: 41
tccattagta gtcgaaattc ttacatatac tacgcagact cagtgaaggg c         51

<210> SEQ ID NO 42
<211> LENGTH: 17
<212> TYPE: PRT
<213> ORGANISM: Homo sapiens

<400> SEQUENCE: 42

Ser Ile Ser Ser Arg Asn Ser Tyr Ile Tyr Tyr Ala Asp Ser Val Lys
 1               5                  10                  15

Gly

<210> SEQ ID NO 43
<211> LENGTH: 18
<212> TYPE: DNA
<213> ORGANISM: Homo sapiens

<400> SEQUENCE: 43
ggccgccttt tcgactac                                              18

<210> SEQ ID NO 44
<211> LENGTH: 6
<212> TYPE: PRT
<213> ORGANISM: Homo sapiens

<400> SEQUENCE: 44

Gly Arg Leu Phe Asp Tyr
 1               5

<210> SEQ ID NO 45
<211> LENGTH: 33
<212> TYPE: DNA
<213> ORGANISM: Homo sapiens

<400> SEQUENCE: 45
cgggctagtc agggcattaa caattattta gcc                             33

<210> SEQ ID NO 46
<211> LENGTH: 11
<212> TYPE: PRT
<213> ORGANISM: Homo sapiens

<400> SEQUENCE: 46

Arg Ala Ser Gln Gly Ile Asn Asn Tyr Leu Ala
 1               5                  10

<210> SEQ ID NO 47
<211> LENGTH: 21
<212> TYPE: DNA
<213> ORGANISM: Homo sapiens

<400> SEQUENCE: 47
agtgcatcca ttttgcaaag t                                          21
```

<210> SEQ ID NO 48
<211> LENGTH: 7
<212> TYPE: PRT
<213> ORGANISM: Homo sapiens

<400> SEQUENCE: 48

Ser Ala Ser Ile Leu Gln Ser
 1               5

<210> SEQ ID NO 49
<211> LENGTH: 27
<212> TYPE: DNA
<213> ORGANISM: Homo sapiens

<400> SEQUENCE: 49
caacaatata attattatcc gctcact                                          27

<210> SEQ ID NO 50
<211> LENGTH: 9
<212> TYPE: PRT
<213> ORGANISM: Homo sapiens

<400> SEQUENCE: 50

Gln Gln Tyr Asn Tyr Tyr Pro Leu Thr
 1               5

<210> SEQ ID NO 51
<211> LENGTH: 24
<212> TYPE: DNA
<213> ORGANISM: Homo sapiens

<400> SEQUENCE: 51
agcagtggtg gttactactg gacc                                             24

<210> SEQ ID NO 52
<211> LENGTH: 8
<212> TYPE: PRT
<213> ORGANISM: Homo sapiens

<400> SEQUENCE: 52

Ser Ser Gly Gly Tyr Tyr Trp Thr
 1               5

<210> SEQ ID NO 53
<211> LENGTH: 51
<212> TYPE: DNA
<213> ORGANISM: Homo sapiens

<400> SEQUENCE: 53
ggatacatct attacagtgg gagcacctcc tacaacccgt ccctcaagag t               51

<210> SEQ ID NO 54
<211> LENGTH: 17
<212> TYPE: PRT
<213> ORGANISM: Homo sapiens

<400> SEQUENCE: 54

Gly Tyr Ile Tyr Tyr Ser Gly Ser Thr Ser Tyr Asn Pro Ser Leu Lys
 1               5                  10                  15

Ser

<210> SEQ ID NO 55

```
<211> LENGTH: 48
<212> TYPE: DNA
<213> ORGANISM: Homo sapiens

<400> SEQUENCE: 55
gagcggggtg agaccggtct atattacccc tattactaca tagacgtc        48

<210> SEQ ID NO 56
<211> LENGTH: 16
<212> TYPE: PRT
<213> ORGANISM: Homo sapiens

<400> SEQUENCE: 56

Glu Arg Gly Glu Thr Gly Leu Tyr Tyr Pro Tyr Tyr Tyr Ile Asp Val
 1               5                  10                  15

<210> SEQ ID NO 57
<211> LENGTH: 42
<212> TYPE: DNA
<213> ORGANISM: Homo sapiens

<400> SEQUENCE: 57
actggaacca gaagtgacgt tggtggttat aactatgtct cc              42

<210> SEQ ID NO 58
<211> LENGTH: 14
<212> TYPE: PRT
<213> ORGANISM: Homo sapiens

<400> SEQUENCE: 58

Thr Gly Thr Arg Ser Asp Val Gly Gly Tyr Asn Tyr Val Ser
 1               5                  10

<210> SEQ ID NO 59
<211> LENGTH: 21
<212> TYPE: DNA
<213> ORGANISM: Homo sapiens

<400> SEQUENCE: 59
gatgtcagta atcggccctc a                                     21

<210> SEQ ID NO 60
<211> LENGTH: 7
<212> TYPE: PRT
<213> ORGANISM: Homo sapiens

<400> SEQUENCE: 60

Asp Val Ser Asn Arg Pro Ser
 1               5

<210> SEQ ID NO 61
<211> LENGTH: 33
<212> TYPE: DNA
<213> ORGANISM: Homo sapiens

<400> SEQUENCE: 61
agctcatata caagcagcag cactctcggg gtg                        33

<210> SEQ ID NO 62
<211> LENGTH: 11
<212> TYPE: PRT
<213> ORGANISM: Homo Sapiens
```

```
<400> SEQUENCE: 62

Ser Ser Tyr Thr Ser Ser Ser Thr Leu Gly Val
1               5                   10
```

ANTI-IDIOTYPIC ANTIBODIES AGAINST ANTIBODIES WHICH INHIBIT THE BINDING OF IMMUNOGLOBULIN E TO ITS HIGH AFFINITY RECEPTORS

The present invention relates to anti-idiotypic antibodies. It is directed towards the inhibition of interactions which would normally cause the triggering of mast cells and basophils induced by cell-bound immunoglobulin E (IgE) linked to an allergen, resulting in the release of histamine and other mediators as well as the de novo synthesis of cytokines involved in the regulation of allergic and inflammatory reactions. It concerns anti-idiotypic antibodies or antibody fragments that interfere with the binding of the C$\epsilon$3 region of IgE to the high affinity receptor for IgE.

Knowledge of specific binding sites on IgE which interact with its high affinity receptor (Fc$\epsilon$RI) provides a basis for the generation of antibodies which prevent this interaction by recognizing the binding epitopes. Induction of such antibodies by vaccination results in a novel and generally applicable therapy for allergy. The present invention describes the identification and production of, in particular, recombinant antibody fragments which can be formulated into a vaccine for the generation of anti-IgE antibodies which protect from induction of IgE-mediated allergic reactions.

Allergic symptoms are induced by the release of vasoactive amines (mediators), notably histamine, from cells into the surrounding tissue and vascular structures. Histamine is normally stored in special cells known as mast cells and basophil granulocytes. The mast cells are dispersed throughout animal tissue whereas the basophils circulate within the vascular system. These cells synthesize and store histamine within the cell unless a specialized sequence of events occurs to trigger its release.

The role of IgE antibodies in mediating allergic reactions is well known. IgE is a complex arrangement of polypeptide chains which, as in other immunoglobulins consists of two light and two heavy chains linked together by disulphide bonds in a "Y" shaped configuration. Each light chain has two domains, one variable ($V_L$) domain linked to a domain with a relatively invariant amino acid sequence termed a constant domain ($C_L$). Heavy chains, by contrast have one variable domain ($V_H$) and in the case of IgE, four constant domains ($C_H1$, $C_H2$, $C_H3$, $C_H4$, also known as C$\epsilon$1, C$\epsilon$2, C$\epsilon$3, C$\epsilon$4). The two "arms" of the antibody are responsible for antigen binding, having regions where the polypeptide structure varies, and are termed Fab' fragments or F(ab')$_2$ which represents two Fab' arms linked together by disulphide bonds. The "tail" or central axis of the antibody contains a fixed or constant sequence of peptides and is termed the Fc fragment. The Fc fragment contains interactive sites which enable the antibody to communicate with other immune system molecules or cells by binding to their Fc receptors. Fc receptors are molecules which bind specifically to active molecular sites within immunoglobulin Fc regions. Fc receptors may exist as integral membrane proteins within a cell's outer plasma membrane or may exist as free "soluble" molecules which freely circulate in blood plasma or other body fluids. In the human system, high affinity binding of IgE to Fc$\epsilon$RI is accomplished by a complex protein—protein interaction involving various parts of the third heavy chain constant region domain (C$\epsilon$3) of IgE and the membrane—proximal immunoglobulin—like domain ($\alpha$2) of the Fc$\epsilon$RI$\alpha$ subunit. Although residues within the C$\epsilon$3 domain of Fc$\epsilon$ and regions belonging to the $\alpha$2 domain of Fc$\epsilon$RI$\alpha$ have been identified which are important for binding, the detailed mechanism of the binding process still remains to be characterized. Experimental evidence has shown that human IgE adopts a bent structure which is speculated to contribute to the high affinity of IgE for Fc$\epsilon$RI (Kd$\cong$10$^{-10}$ M). Moreover, this bent structure is also postulated to be responsible for the equimolar complex between IgE and cell bound or soluble Fc$\epsilon$RI$\alpha$, although the IgE molecule would provide identical epitopes on the two C$\epsilon$3 domains for receptor binding. This monovalency is a functional necessity if receptor triggering in the absence of allergen is to be avoided.

Interactive sites, depending on their function, may already be exposed and therefore able to bind to cellular receptors. Alternatively, they may be hidden until the antibody binds to the antigen, whereupon the antibody may change in structure and subsequently expose other active sites which can then trigger a specific immune activity. A conformational rearrangement affecting C$\epsilon$3 upon receptor binding has been proposed as an explanation for the 1:1 stoichiometry of the Fc$\epsilon$/Fc$\epsilon$RI complex on the cellular surface.

The allergic (immunologic) release of mediators within the organism from the mast cells and basophils can only occur under the following circumstances: an IgE molecule must lock onto or attach itself with its Fc portion to the cellular Fc receptor site, thus securing the IgE molecule to the mast cell or basophil; and the Fab' portions of the cell-bound IgE molecules must be cross-linked by a particular compatible antigen (the allergen). Should such an interaction occur, the mast cell or basophil is automatically triggered to release histamine to the local environment, manifesting familiar allergic symptoms (FIG. 1). Other biochemical events follow in a late phase reaction, resulting in de novo synthesis and release of cytokines and other mediators.

Conventional approaches to allergy treatment have involved systemic therapy with anti-histamines or attempts to desensitize patients, approaches which have not adressed themselves to the basic IgE-mast cell/basophil interaction. Another approach has concerned itself with the production of polypeptide chains capable of blocking the binding of the IgE antibody to the Fc receptors on the cell surfaces and displacing IgE from binding sites upon which IgE is already bound, and investigated the nature of a putative "effector" site within the IgE Fc region which was speculated to provide an immunological signal which triggers mast cells/basophils for histamine release.

Using recombinant IgE fragments as immunogens for the generation of a protective anti-IgE vaccine has also been tried and shown to be effective. The main objection against such a vaccine results from the possibility that using large IgE fragments for immunization could initiate not only the production of inhibitory antibodies but also generate crosslinking and thereby anaphylactogenic antibodies in the patients.

A strategy to overcome this problem would aim at the identification of the smallest IgE fragment possible, ideally consisting of the receptor binding site only, which is buried within the IgE/IgERI complex after binding and therefore no longer accessible for crosslinking by the vaccine-generated immune response. Although attempts are still made this strategy is unlikely to be successful in view of the spatial distances of the various C$\epsilon$3 regions involved in IgE/IgERI interaction.

The problems intrinsically linked to the "classical" vaccine approach may be overcome by using short mimotope peptides for active immunization, either as chemically synthesized peptides coupled to appropriate carriers, or as recombinant fusion constructs with e.g. ovalbumin or IgG. Such peptides are structural mimics of the epitope recognized by monoclonal antibody BSW17, which recognizes a conformational epitope on Fcε with a part of it residing within Cε3 and part of it residing within Cε4. The hybridoma cell line producing BSW17 has been deposited on Dec. 19, 1996 with the Center For Applied Microbiology and Research, European Collection of Cell Cultures located at Porton Down, Salisbury, United Kingdom, SP4OJG under the accession number 96121916.

The present invention avoids the possible disadvantages intrinsic to a mimotope peptide approach. It is based upon antibodies or antibody fragments which are anti-idiotypic to antibodies that interfere with IgE-binding to its high affinity receptor, in particular upon a recombinant anti-idiotypic antibody to BSW17. According to Jerne's network theory (Jerne N., *Ann. Immunol.* 125C [1974] 373), hypervariable regions of an antibody (Ab1) can themselves act as antigens. The antibodies produced in this way are known as anti-idiotype (anti-id) antibodies (Ab2) since they bind to the idiotypic region of the first antibody (FIG. 3). Such anti-id antibodies are directed to the binding site (paratope) of the first antibody (Ab1) and thus represent an "internal image" of the original antigen. Consequently, the anti-id antibodies (Ab2), termed internal image antibodies or Ab2β, are also capable of eliciting antibody formation via their hypervariable regions. These anti-anti-id antibodies (Ab3) structurally mimic the paratope of Ab1 and therefore have similar biological properties as the Ab1 antibody. In case of the hIgE/BSW17 system, IgE represents the original antigen and BSW17 the antibody Ab1. The paratope of an anti-BSW17 idiotype antibody Ab2 therefore represents a structural mimic of the hIgE region (the epitope) recognized by BSW17. Structurally, the Ab2 paratope is equivalent to the chemically synthesized BSW17 mimotope peptides mentioned above. If such a (recombinant) anti-BSW17 idiotype antibody is used as a vaccine, a BSW17-like immune response (Ab3) will be induced in the vaccinated patient. Like BSW17, these (polyclonal) Ab3 immunoglobulins will interfere with the binding between IgE and its high affinity receptor, thus acting as anti-allergic agents. In contrast to flexible synthetic mimotope peptides, the Ab2 paratope will be presented to the environment in a structurally defined conformation. The immune reaction directed against the defined hIgE epitope will therefore be more specific. Moreover, no heterologous immunogenic carrier protein will be necessary. Possible side effects caused by a protein carrier like tetanus toxoid or diphteria toxoid, will therefore be avoided.

The present invention comprises antibodies or antibody fragments which are anti-idiotypic to antibodies such as E25 (olizumab) or CGP56901 or preferably, BSW17 that interfere with the binding of the Cε3 region of IgE to the high affinity receptor for IgE; they are hereinafter briefly named "the mimobodies of the invention". When they are anti-idiotypic to BSW17 they are hereinafter briefly named "BSW17-mimobodies".

The mimobodies of the invention are thus anti-idiotype antibodies or antibody fragments which specifically bind to an epitope that is the paratope of an anti-IgE antibody which recognizes the site on the Cε3 region of the IgE molecule that binds to the high affinity receptor for IgE (FcεRI).

The mimobodies of the invention are in principle of human origin, insofar as use in humans is contemplated. They preferably are recombinant. They preferably are monoclonal. They preferably are antibody fragments, e.g. consisting of or comprising:

either both heavy and light chains (e.g. Fab fragments), or single heavy or light chains (e.g. light chain dimers), preferably together with their constant region component stretches, e.g. as defined in FIG. 4 (Seq.id. no. 35, 36, 37 and 38), whereby "constant region" is to be understood as also covering minor steric modifications, such as found in allotypic variants, e.g. at 1 to 5, normally just one, amino acid position in the constant part;

or parts thereof, in particular at least the specificity-determining parts thereof, e.g. as defined in FIGS. 5a to 5d (Seq.id. no. 2, 4, 6, 8);

or subparts thereof, in particular at least the hypervariable subparts thereof, such as peptides made up of stretches of amino acids comprising at least one CDR, e.g. comprising at least one CDR, or preferably two, or more preferably the three CDR of FIG. 5a, 5b, 5c or 5d (Seq.id. no. 2, 4, 6, 8), optionally together with adjacent framework sequences, e.g. of up to about 10 amino acids at one or both CDR ends.

The mimobodies of the invention represent isolated and substantially pure antibodies or antibody fragments derived from naturally-occurring anti-id anti-IgE antibodies. In particular, they are substantially free of other antibodies. Under "substantially pure" is to be understood a purity of at least about 60% by weight, preferably about 90% by weight, more preferably about 99% by weight or more.

The invention also concerns pharmaceutical compositions, especially vaccines, comprising mimobodies of the invention, either as a single molecular entity or as a protein conjugate chemically coupled to an immunogenic carrier molecule, where appropriate together with an adjuvant and further conventional excipients.

It further concerns the mimobodies of the invention for use as a pharmaceutical, in particular as a vaccine, in particular in the treatment of IgE-mediated diseases.

It further concerns the use of antibodies that interfere with the binding of the Cε3 region of IgE to the high affinity receptor for IgE, such as BSW17, for the identification of mimobodies of the invention, using conventional methods, such as phage display technology.

It further concerns a method of treatment of IgE-mediated diseases by, in particular, vaccination, comprising administration of a therapeutically effective amount of the mimobodies of the invention to a patient in need of such treatment or vaccination.

It further concerns the use of the mimobodies of the invention in the preparation of a medicament against IgE-mediated diseases, in particular of a vaccine.

It further concerns the use of the mimobodies of the invention for raising polyclonal or monoclonal antibodies thereagainst for passive immunization; the preparation of polyclonal or monoclonal antibodies against mimobodies of the invention for passive immunization, either by administration of mimobodies of the invention to a suitable non-human animal and isolation and purification of the antibodies generated thereagainst, or by conventional hybridoma technology; and the use of polyclonal or monoclonal antibodies whenever obtained from mimobodies of the invention in the treatment of IgE-mediated diseases by passive immunization.

It further concerns a process for the identification of the mimobodies of the invention which comprises identifying naturally occurring anti-idiotypic anti-IgE antibodies;

isolating fragments thereof; and selecting recombinant fragments thereof by binding to a suitable anti-IgE monoclonal antibody, such as BSW17, which interferes with the binding of the Cε3 region of IgE to the high affinity receptor for IgE.

Once identified and characterized, the mimobodies of the invention may be prepared in conventional manner, e.g. by recombinant DNA technology or chemical synthesis.

For the identification of anti-idiotypic antibodies displaying the same specificity as the mimotope peptides mentioned above (i.e. the selected epitope on IgE), a bacteriophage display library can be used which is expressing the Fab part of a human antibody repertoire. This library is constructed e.g. from a pool of B cells obtained from tonsils of human subjects, and immobilized BSW17 antibody used as target for biopanning. Human Fab-expressing phage particles are isolated and enriched that specifically recognize BSW17. Thus these recombinant Fab fragments are mimobodies of the invention and represent anti-idiotypes against the hypervariable regions of BSW17. When used as a vaccine, they induce an immune response which results in the production of BSW17-like antibodies in the allergic patient. Since BSW17 is non-anaphylactogenic and inhibitory to IgE/IgERI binding and IgE synthesis on B cells, the polyclonal antibodies raised in the patient against the BSW17 anti-idiotypic Fab vaccine have similar properties. The immune response is very specific and safe since, in contrast to the "classical vaccine approach", no IgE-derived protein fragments are present which could generate crosslinking antibodies in the immunized patients, and compositions can be contemplated which are devoid of carrier.

These BSW17-mimobodies are recombinant antibodies or antibody fragments consisting of variable domains (V-domains) and constant domains (C-domains) derived from human immunoglobulin G. Two different clones (clones 52 and 43), which display different mimobody fragments on their surface, have been identified by biopanning of antibody phage libraries on immobilized BSW17 antibody. The mimobody structure which mimics the BSW17 epitope on human IgE resides within the hypervariable regions (CDR) and adjacent framework regions (FR) of the V-domains. The cDNA and amino acid sequences of the heavy and light chain V-domains of clone 52 and clone 43 are shown in FIGS. 5a to 5d (Seq.id.no. 1 to 8). The clone 52 light chain construct (L.C.)$_2$ consists of a dimeric "Fab-like" light chain fragment. The full structure of these BSW17-mimobodies is represented schematically in FIG. 4A to 4C, whereby the constant region parts thereof should be understood as also covering minor steric modifications such as found in allotypic variants as mentioned above. The amino acid sequence for each complete heavy and light chain of these clones is provided in FIGS. 12a to 12d (Seq.id. no. 35 to 38).

The mimobodies of the invention possess pharmacological activity. They are therefore indicated for use as pharmaceuticals, e.g. as antigens for vaccines. While being substantially incapable of mediating non-cytolytic histamine release, they are capable of eliciting antibodies with strong serological cross-reactivity with the target amino acid sequences of the Fc region of IgE.

The initial dose of mimobody of the invention is e.g. from about 0.05 mg to about 5 mg, preferably about 1 mg; it will be administered e.g. nasally, or subcutaneously or intramuscularly, followed by repeat (booster) doses of the same, e.g. 14 to 28 days later. Dosages to be used will depend to some extent on the age, weight and general health of the patient and may be adjusted as appropriate.

Direct vaccination, namely active immunization with the mimobodies of the invention will preferably be carried out using recombinant peptides (Fab fragment, light chain or heavy chain) which can be produced in various host expression systems, e.g. bacteria, fungi or eukaryotic cells in conventional manner.

The administration of free recombinant mimobody is preferred. However, it is also possible to increase the immunogenicity of the immunogen further by chemical coupling to a immunogenic carrier. The term "immunogenic carrier material" herein includes those materials which have the property of independently eliciting an immunogenic response in a host animal and which can be covalently coupled to polypeptide either directly via formation of peptide or ester bonds between free carboxyl, amino or hydroxyl groups in the polypeptide and corresponding groups on the immunogenic carrier material or alternatively by bonding through a conventional bifunctional linking group. Examples of such carriers include albumins of animal sera, globulins of animal sera, thyroglobulins of animals, hemoglobins of animals, hemocyanins of animals (particularly Keyhole Limpet Hemocyanin [KLH]), proteins extracted from ascaris, e.g. ascaris extracts such as those described in *J. Immun.* 111 [1973] 260–268, *J. Immun.* 122 [1979] 302–308, *J. Immun.* 98 [1967] 893–900 and *Am. J. Physiol.* 199 [1960] 575–578, or purified products thereof; polylysine, polyglutamic acid, lysine-glutamic acid copolymers, copolymers containing lysine or ornithine, etc. Recently, vaccines have been produced using diphteria toxoid such as CRM197 or tetanus toxoid as immunogenic carrier materials (Lepow. M. L., et al., *J. Infectious Diseases* 150 [1984] 402–406; and Coen Beuvery, E. et al., *Infection and Immunity* 40 [1983] 39–45) and these toxoid materials can also be used herein. In contrast to chemically detoxified diphteria toxin, the recombinant mutated diphteria toxin CRM197 is preferably used. In CRM197 the glycine-52 residue is replaced by glutamic acid, resulting in a non toxic product. CRM197 is a well characterized non-toxic carrier protein and is used in a registered human vaccine. The purified protein derivative of tuberculin (PPD) may also be used in the "active" immunization scheme since:

(1) it does not induce a T-cell response itself (i.e. it is in effect a "T-cell hapten"), and yet it behaves as a fully processed antigen and is recognized by T-cells as such; (2) it is known to be one of the most powerful hapten "carriers" in the linked recognition mode; and (3) it can be used in humans without further testing.

As hapten-carrier binding agents, those conventionally employed in the preparation of antigens can be employed. The covalent coupling of the mimobodies of the invention to the immunogenic carrier material can be carried out in conventional manner. For example, for direct covalent coupling it is possible to utilize bis-N-succinimidyl derivatives, most preferably bis(sulfosuccininidyl)suberate as coupling agent, or glutaraldehyde or carbodiinmide, most preferably (dicyclohexyl)carbodiimide or 1-ethyl-3-(3-dimethylamino-propyl)carbodiimide.

The ratios of hapten, hapten-carrier binding agent and carrier can be appropriately determined but it is preferred that the carrier be in an amount of about 1 to about 6 times, preferably about 1 to about 5 times the weight of the hapten, and the hapten-carrier binding agent be in an amount of about 5 to about 10 times the molar equivalent of the hapten. By the above coupling reaction, the carrier is bound to the hapten via the hapten-carrier binding agent to obtain a desired antigen composed of a peptide-carrier complex of mimotope of the invention and carrier.

After completion of the reaction, the resultant immunogen can be isolated and purified in conventional manner, such as by dialysis, gel filtration or fractionation precipitation.

The present invention is essentially directed to active immunization by direct vaccination; however, it also contemplates passive immunization. In such situation, mimobodies of the invention are administered to a suitable non-human animal and antibodies generated thereagainst are isolated and purified, and subsequently administered to a human subject for inducing alleviation of allergic symptoms.

The mimobodies of the invention are indicated for use as pharmaceuticals, especially vaccines, in particular in the treatment of IgE-mediated diseases, such as allergy, e.g. asthma, atopic dermatitis, allergic forms of eosinophulia, rhinitis, chronic urticaria and food allergies.

"Treatment" is to be understood as comprising prophylactic as well as curative treatment. The host is preferably human, but the invention is applicable mutatis mutandis to essentially any mammal e.g. a cat or a dog.

Figure 1:
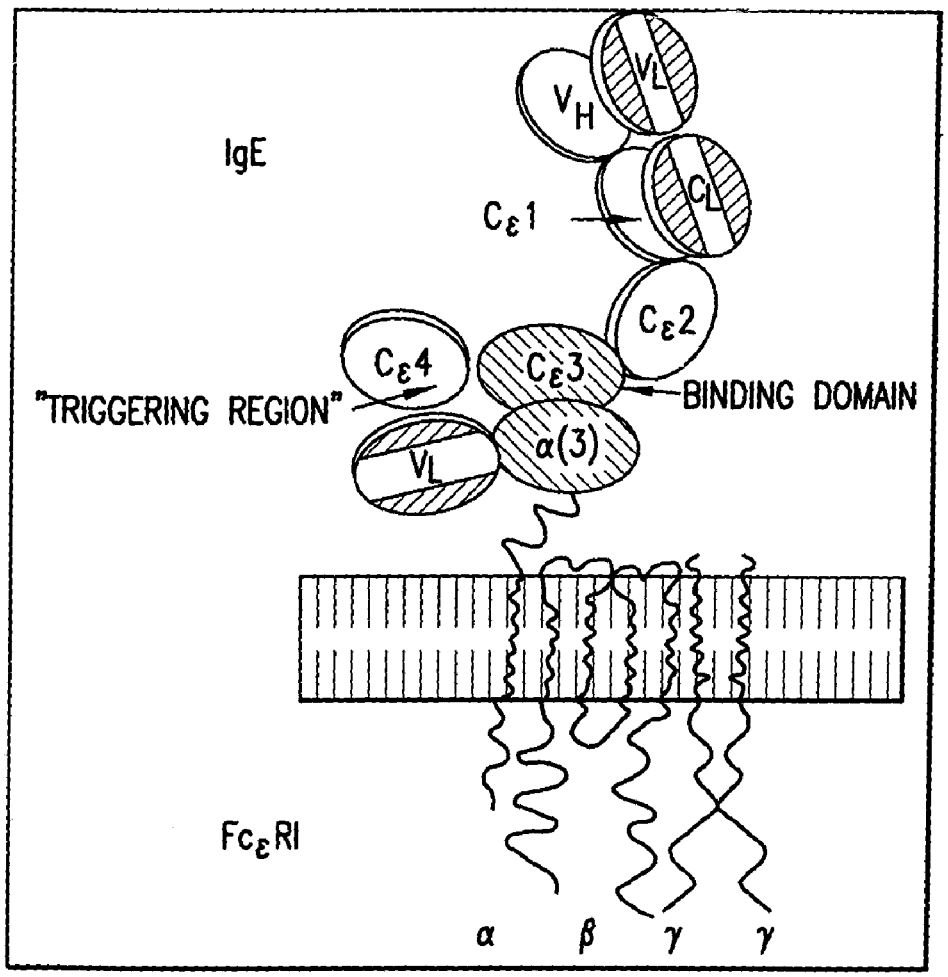
FIG. 1: Interaction between IgE and its high affinity receptor.
Figure 2:
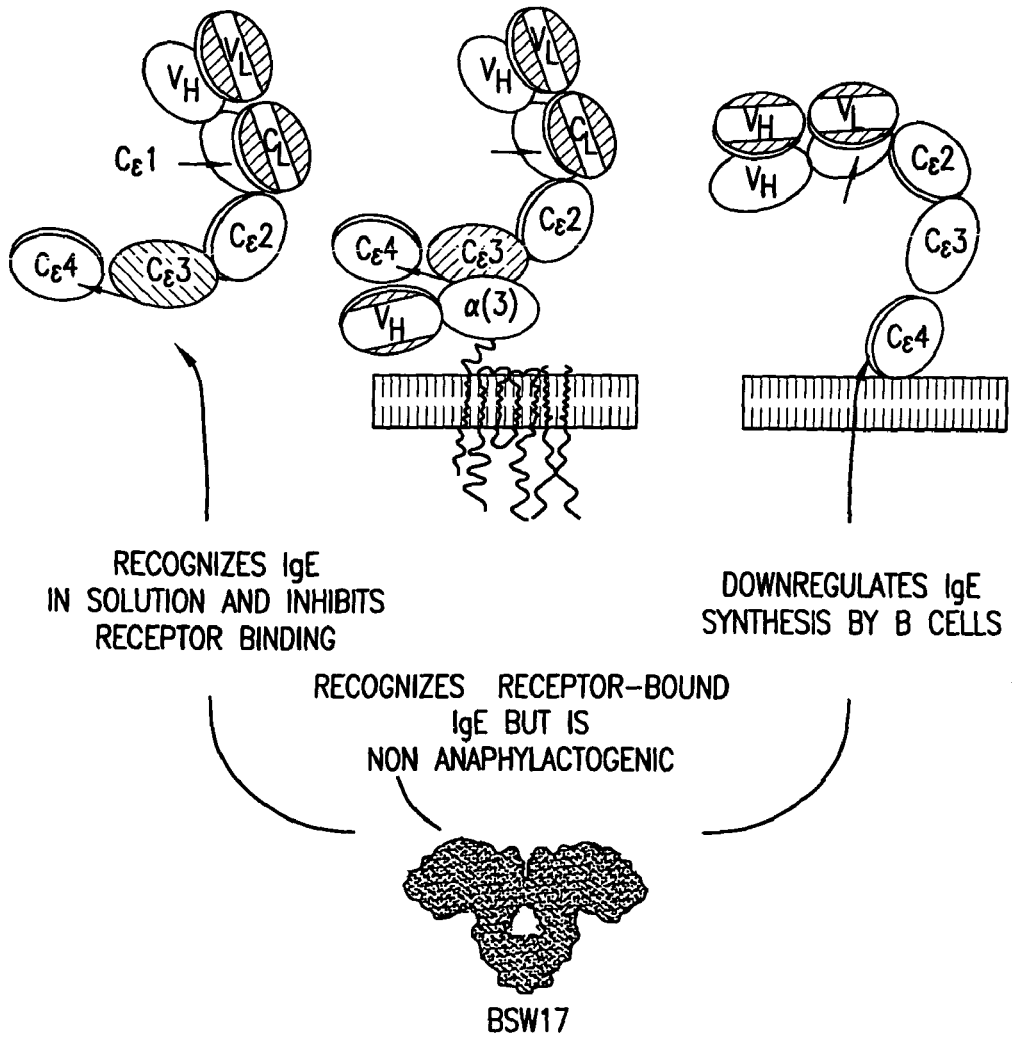
FIG. 2: Properties of the monoclonal anti-hIgE antibody BSW17.
Figure 3:
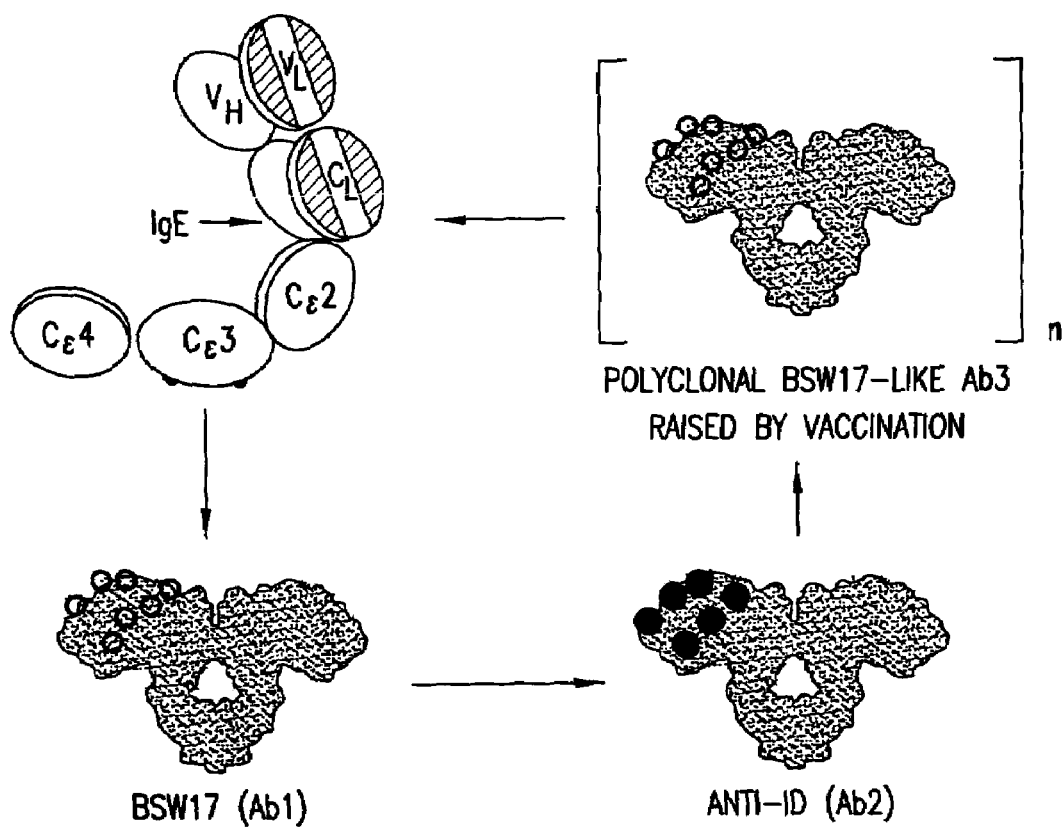
FIG. 3: The anti-idiotypic network.

The hIgE epitope recognized by BSW 17 and the anti-idiotypic paratope are schematically indicated as black dots. Black circles indicate the homologous hypervariable regions of antibody BSW17 (Ab1) and polyclonal antibodies 3 (Ab3), induced by immunization with the anti-idiotypic antibody Ab2.

FIG. 4: Structure of three recombinant BSW17 mimobodies:

| A: Anti-id-BSW17, clone 52 (SDS426); light chain: | (L.C.)$_2$ | (Seq.id. no. 36) |
|---|---|---|
| B: Anti-id-BSW17, clone 52 (SDS427); Fab: | F$_{AB}$ | (Seq.id. no. 35 and 36) |
| C: Anti-id-BSW17, clone 43 (SDS463); Fab: | F$_{AB}$ | (Seq.id. no. 37 and 38) |

FIG. 5: Anti-BSW17 Fab clones: DNA sequence of bacteriophage-displayed human immunoglobulin and deduced amino acid sequence:

Hypervariable regions (Complementarity Determining Regions; CDR) are in bold italics:

FIG. 5a: clone 52; variable heavy chain (Seq.id.no. 1 and 2) (CDR1: Seq.id.no. 39 and 40; CDR2: Seq.id.no. 41 and 42; CDR3: Seq.id. no. 43 and 44);

FIG. 5b: clone 52; variable light chain (Seq.id.no. 3 and 4) (CDR1: Seq.id.no. 45 and 46; CDR2: Seq.id.no. 47 and 48; CDR3: Seq.id.no. 49 and 50);

FIG. 5c: clone 43; variable heavy chain (Seq.id.no. S and 6) (CDR1: Seq.id.no. Si and 52; CDR2: Seq.id.no. 53 and 54; CDR3: Seq.id.no. 55 and 56);

FIG. 5d: clone 43; variable light chain (Seq.id.no. 7 and 8) (CDR1: Seq.id.no. 57 and 58; CDR2: Seq.id.no. 59 and 60; CDR3: Seq.id.no. 61 and 62).

FIG. 6: Amino acid sequence homology between anti-BSW17 rFab and the Cε3 domain of human IgE:

A: anti-id Fab, clone 52, heavy chain (hIGE,Cε3: Seq.id.no. 25; clone 52: Seq.id.no.26);

anti-id Fab, clone 52, light chain, alignment 1 (IGE,Cε3: Seq.id.no. 27;
clone 52: Seq.id.no.28);
anti-id Fab, clone 52, light chain, alignment 2 (hIGE,Cε3: Seq.id.no. 29;
clone 52: Seq.id.no.30), respectively.;

B: anti-id Fab, clone 43, heavy chain (hIGE,Cε3: Seq.id.no. 31; clone 43: Seq.id.no.32);
anti-id Fab, clone 43, light chain (hIGE,Cε3: Seq.id.no. 33; clone 43: Seq.id.no.34), respectively.

Amino acid sequence alignment: identical residues are shown in black boxes, similar amino acids are in gray boxes (Lipman and Pearson). The positions of Fcε residues are indicated on top of each alignment. The contribution of hypervariable (CDR) and framework regions (FR) of the recombinant Fab fragments are shown below each pair of sequences.

Figure 7:
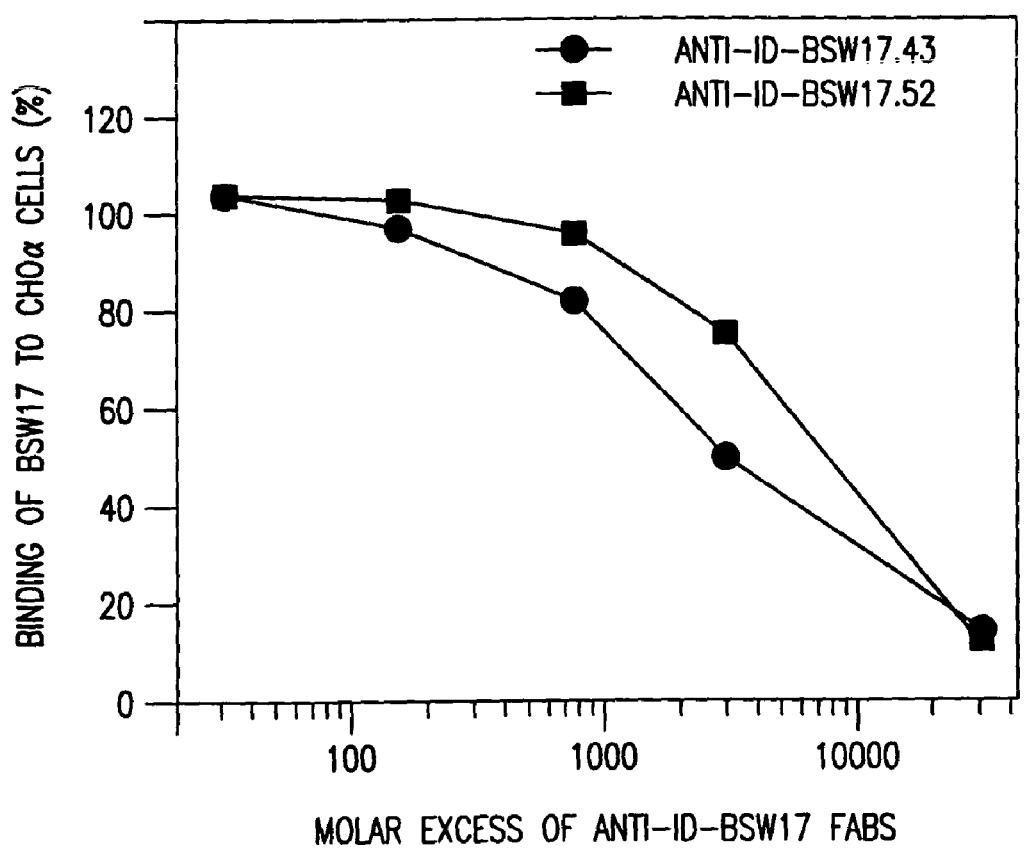

FIG. 7: Competitive binding of anti-id BSW17 rFab on IgE-primed CHOP cells with FITC-labeled BSW17

Figure 8:
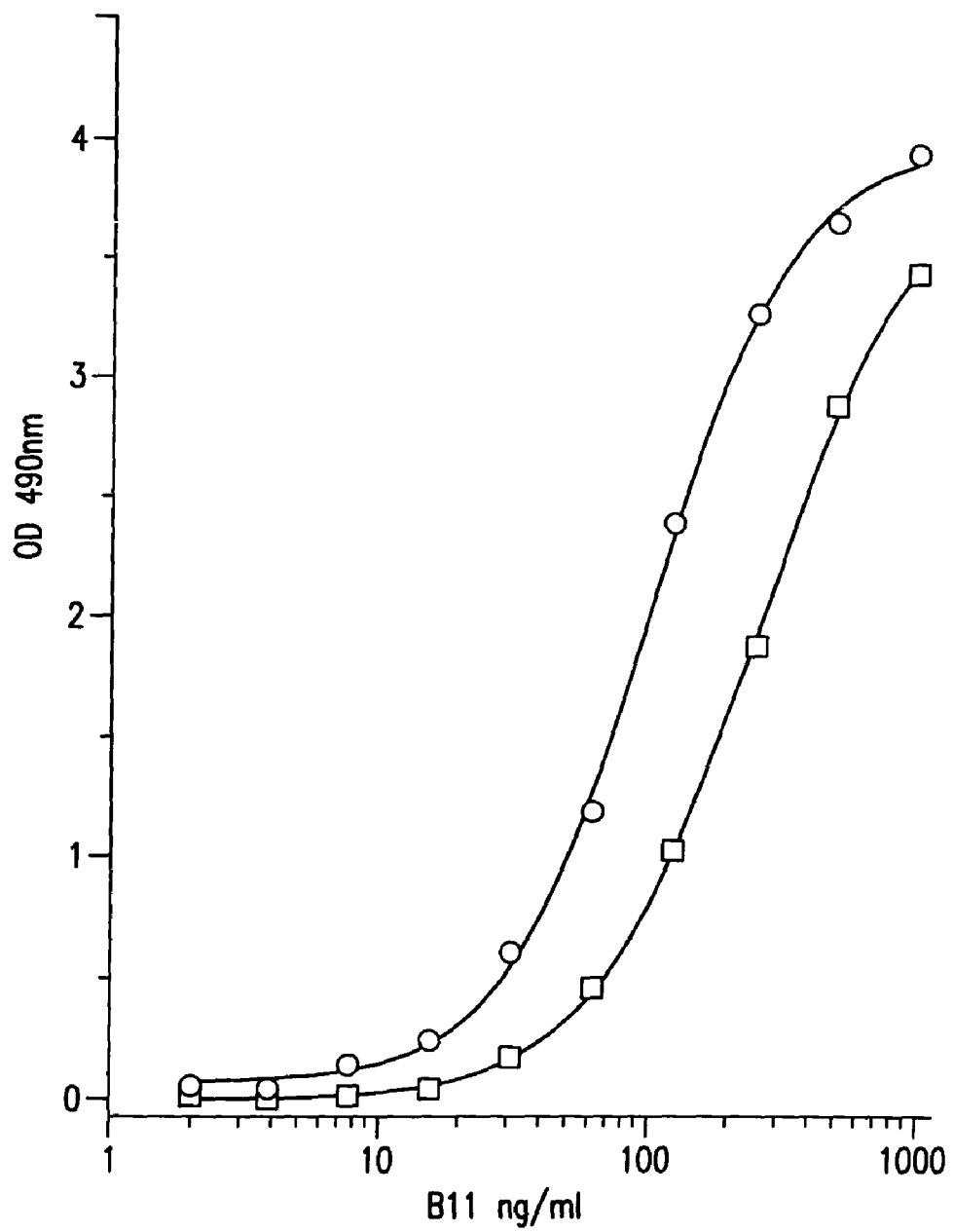

FIG. 8: Binding of affinity-purified rabbit anti-BSW17 mimobody immunoglobulins to human IgE:

Determination of hIgE/anti-mimobody complexes by sandwich-ELISA: hIgE and immunoaffinity-purified anti-BSW17 mimobody preparations were mixed at equimolar concentration and incubated overnight at 4° C. The incubation mixtures were subsequently added to microtiter plate wells coated with monoclonal anti-hIgE antibody LE27 (1 µg/ml) as capturing antibody. Bound mimobody IgG was detected with goat anti-rabbit IgG-HRP:

☐=hIgE/SDS410 complexes;
◯=hIgE/SDS411 complexes.

FIG. 9: Anti-BSW17 mimobody immune response in Balb/c mice:

■=mouse 1; ●=mouse 2; ▼=mouse 3; ▲=mouse 4; ◆=mouse 5

A: anti-id-BSW17.52; light chain (SDS426);
B: anti-id-BSW17.52; Fab (SDS427);
C: anti-id-BSW17.43; Fab (SDS463);

O.D. values represent the optical density readouts, corrected for background binding to non-coated wells. Mean values of measurements in duplicate are shown. Variations were generally <0.05 O.D.

Figure 10A:
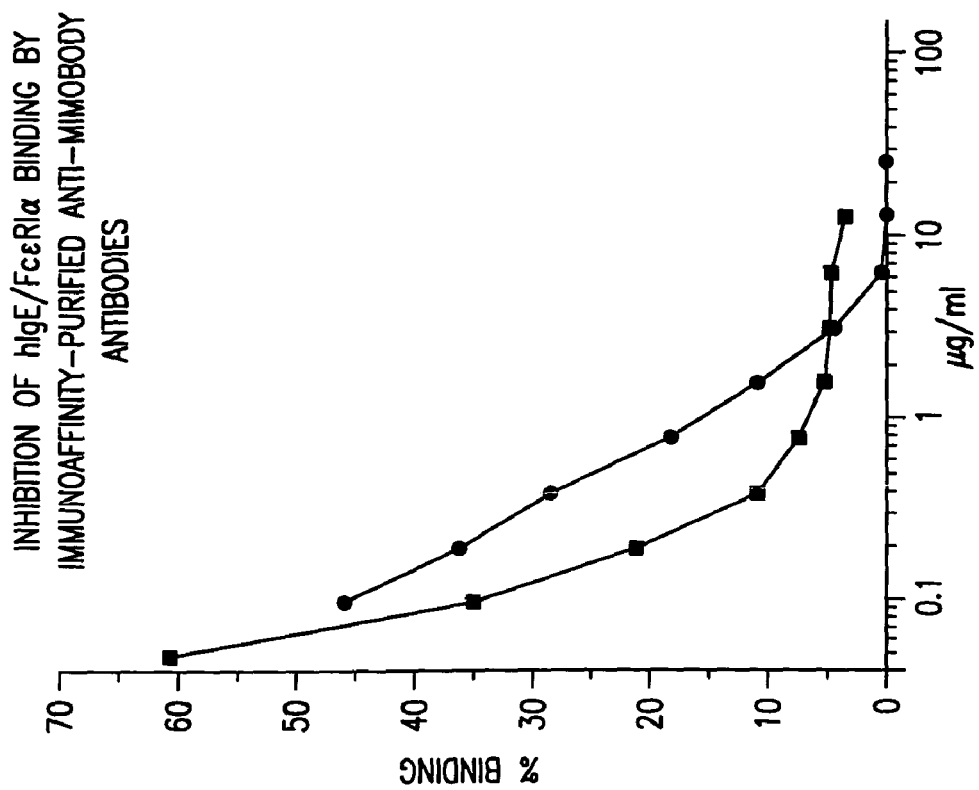
Figure 10B:
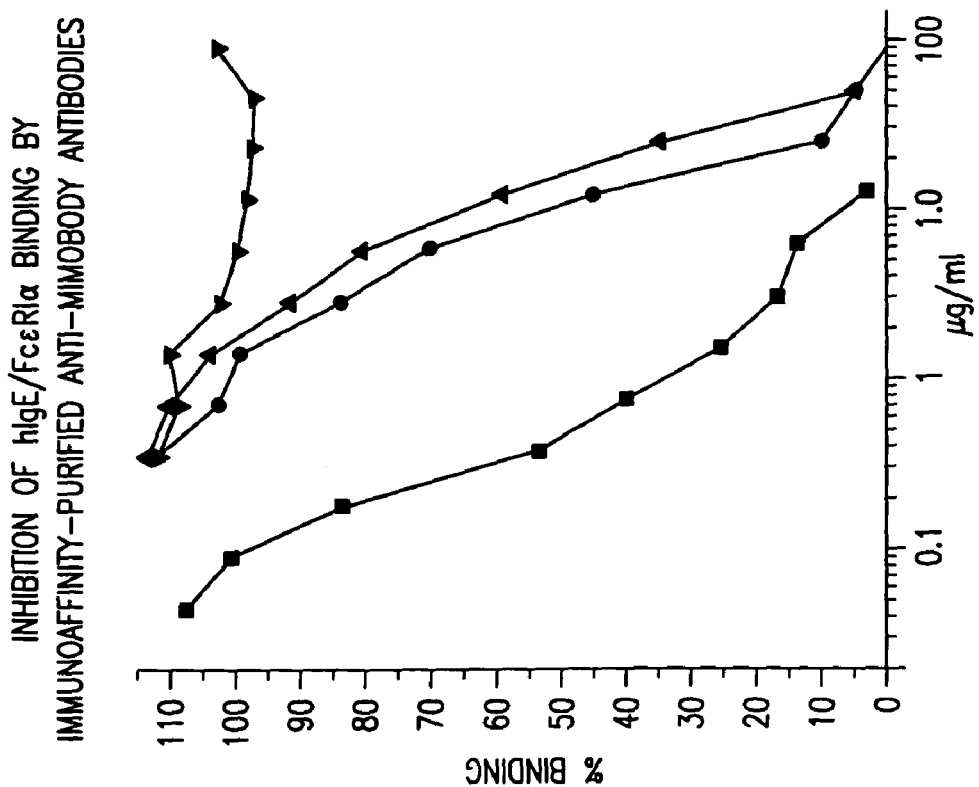

FIG. 10: Inhibition of HIgE/FcεRIα binding by immunoaffinity-purified anti-mimobody antibodies:

A: ■=BSW17
●=anti-clone 52; light chain (SDS410)
Δ=anti-clone 52; Fab (SDS411)
▼=anti-clone 52; light chain (column flowthrough)
B: ■=BSW17
●=anti-clone 43 Fab (SDS476)

Figures 11A, 11B:
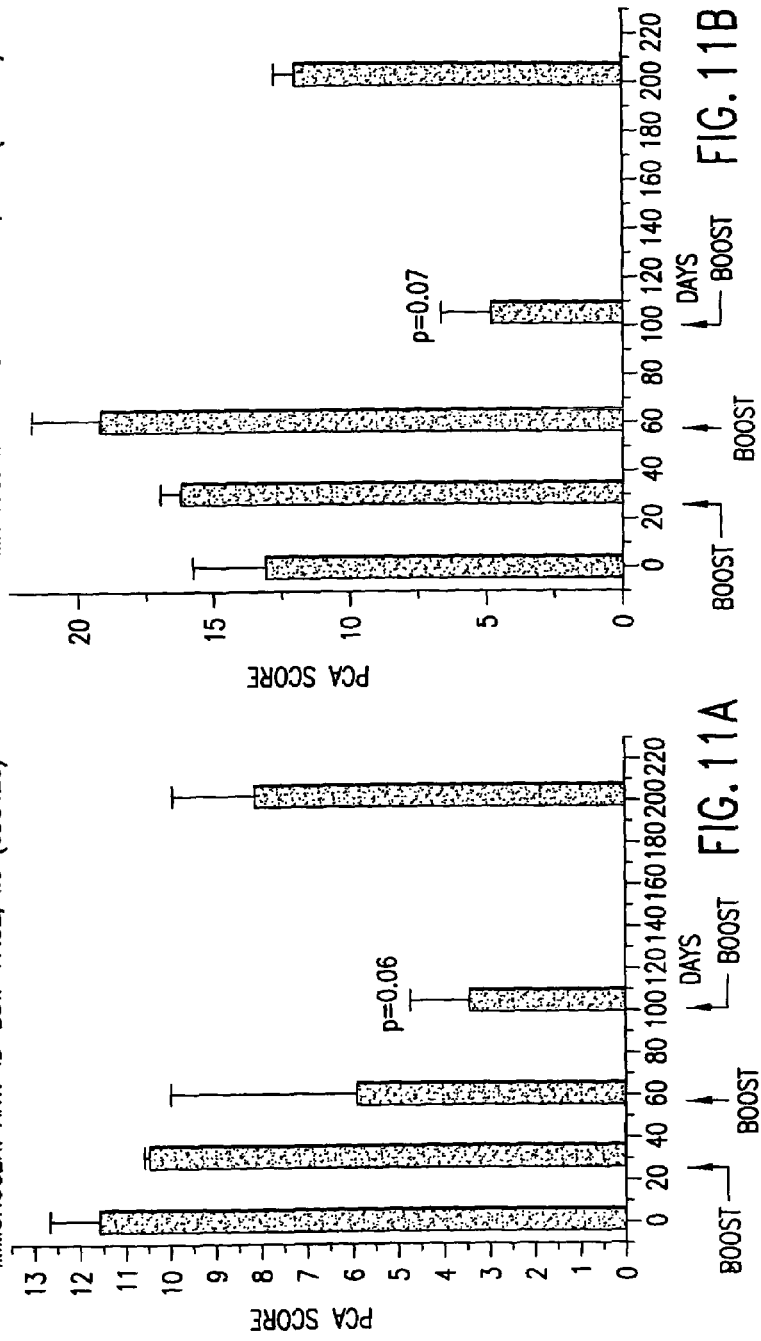
Figure 11C:
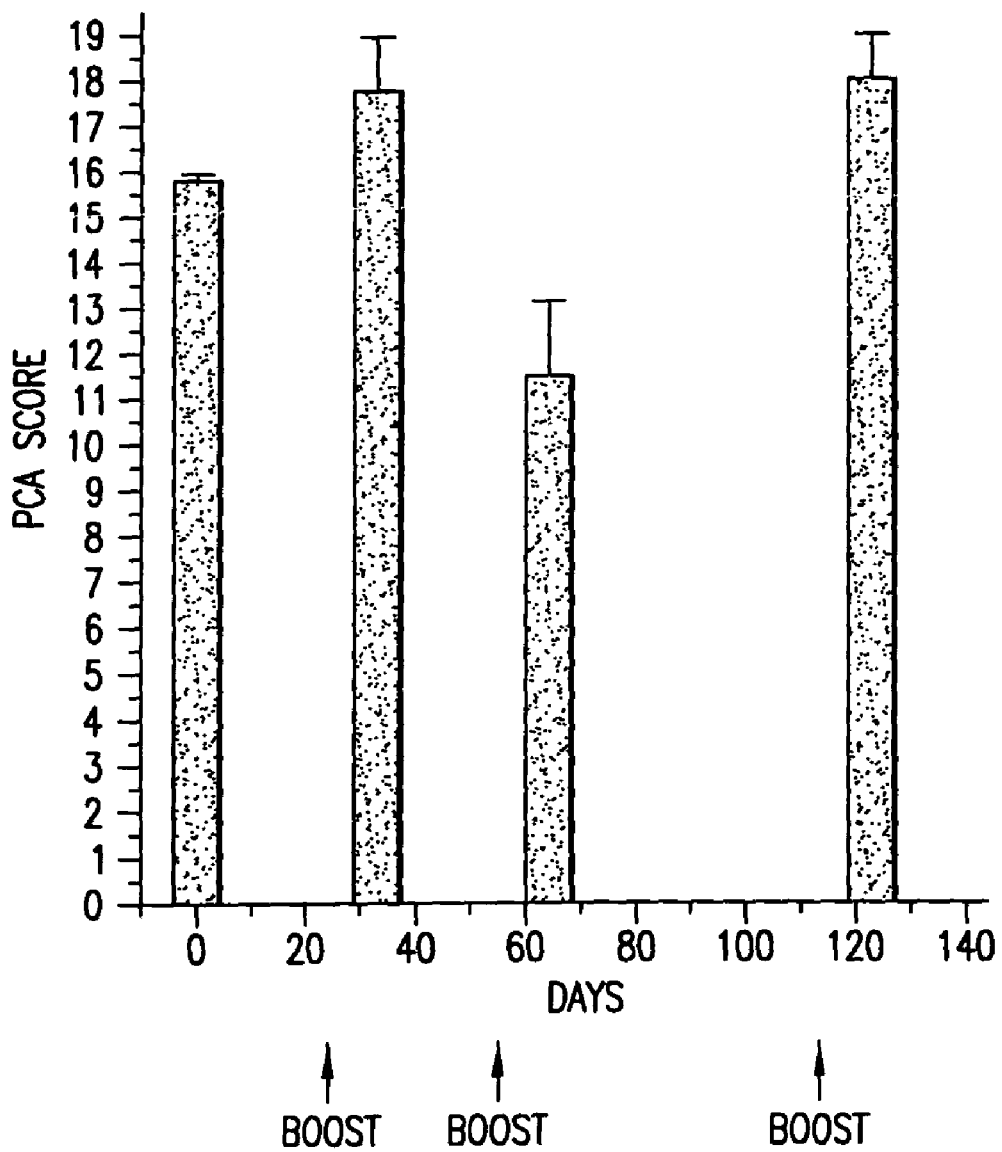

FIG. 11: PCA score profiles of rhesus monkey groups (n=2), immunized with various mimobody preparations:

A: Immunogen: anti-id-BSW17.52; light chain (SDS426);
B: Immunogen: anti-id-BSW17.52; Fab (SDS427);
C: Immunogen: anti-id-BSW17.43; Fab (SDS463).

Passive cutaneous anaphylaxis (PCA) reaction in rhesus monkey skin at various time points after immunization. PCA score values represent PCA intensities calculated from the area under the curves (AUC) generated by plotting the diameters of the blue skin dots against the injected IgE (JW8) concentrations. Scores are average numbers for each group of two monkeys immunized with the same mimobody preparation, calculated from the single monkey values shown in Table 4. Variations are shown as error bars. Statistical p values are indicated above error bars. Time points of boosting injections are indicated below the x-axis.

Figure 12B:
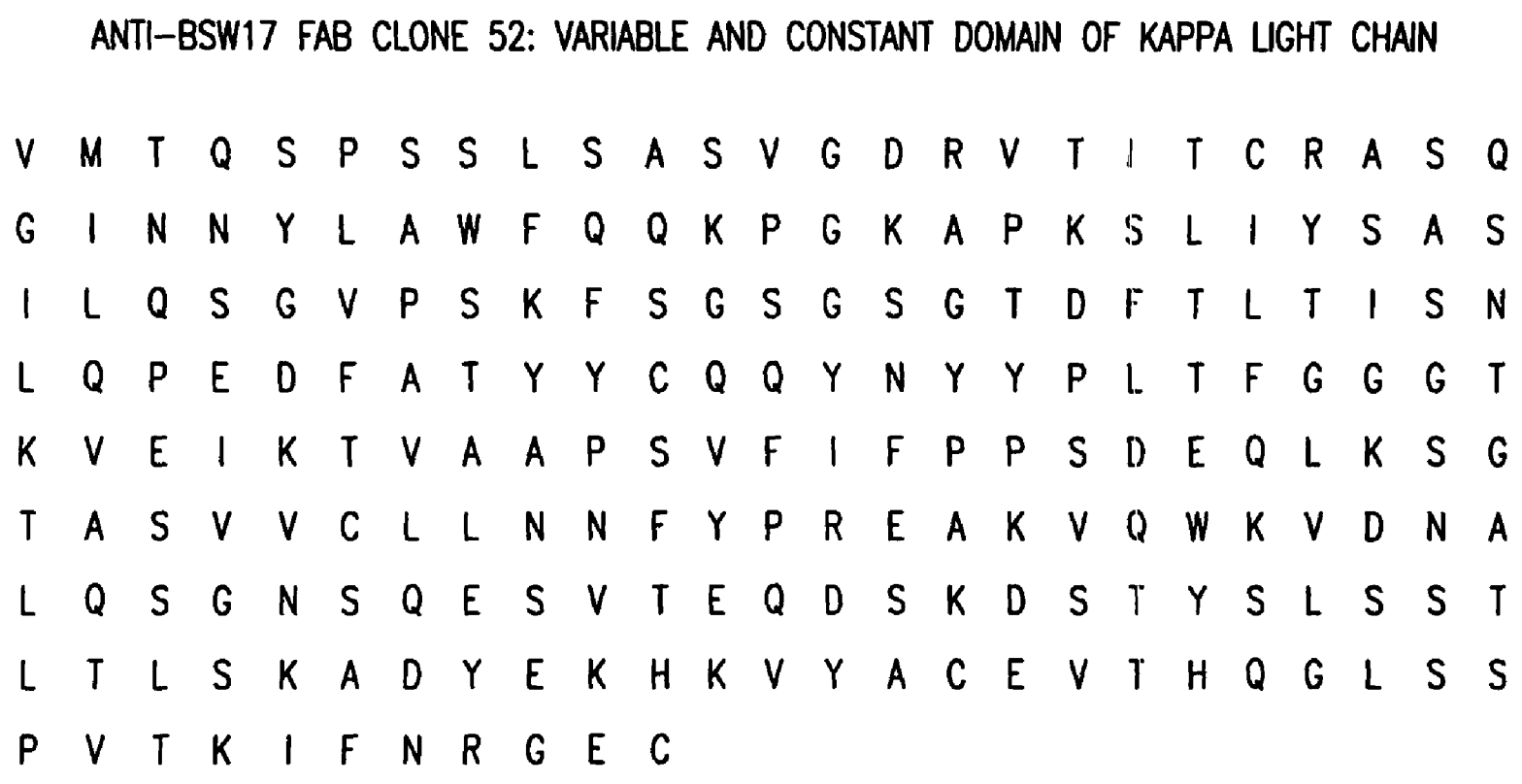
Figure 12C:
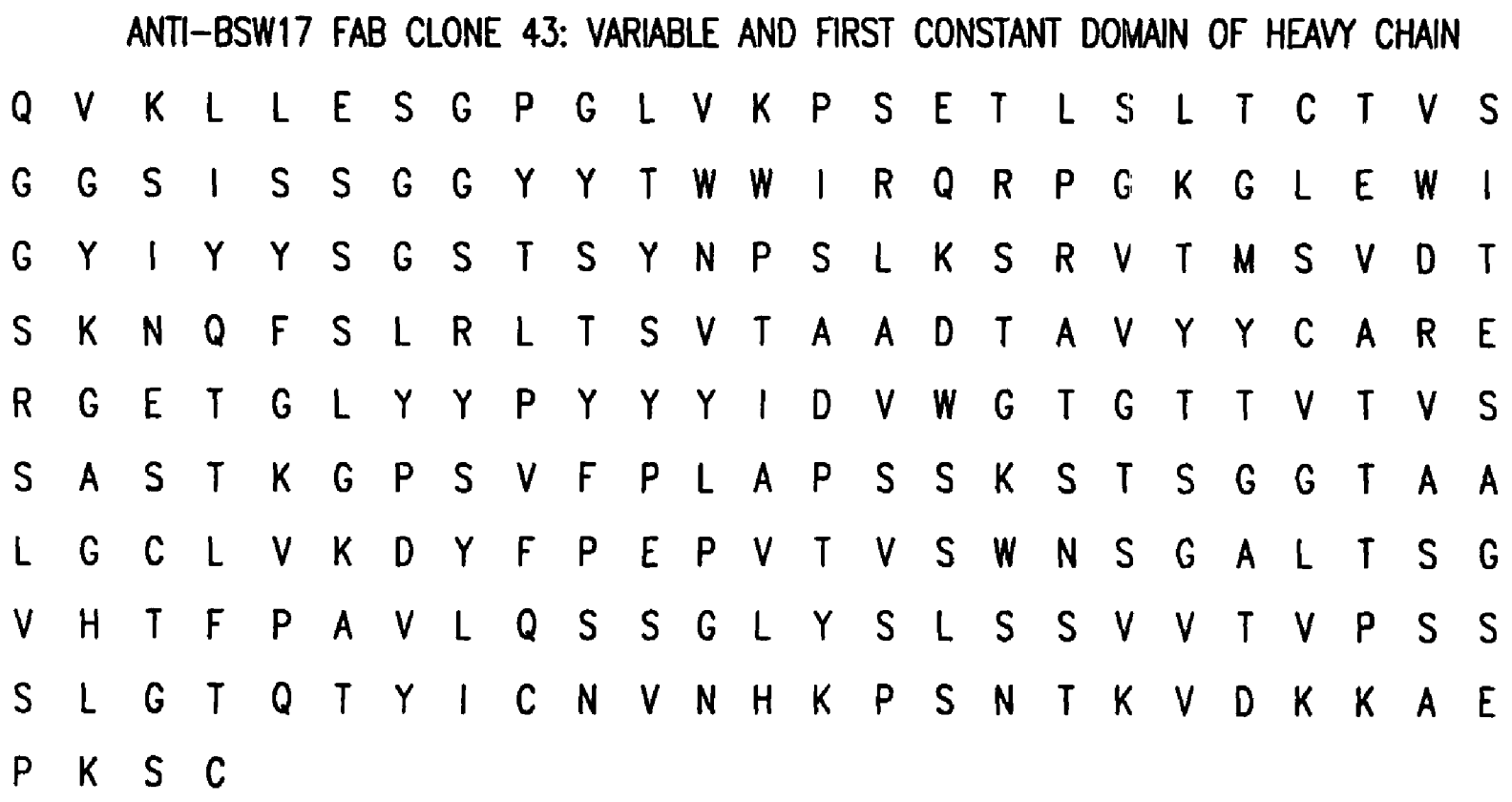
Figure 12D:
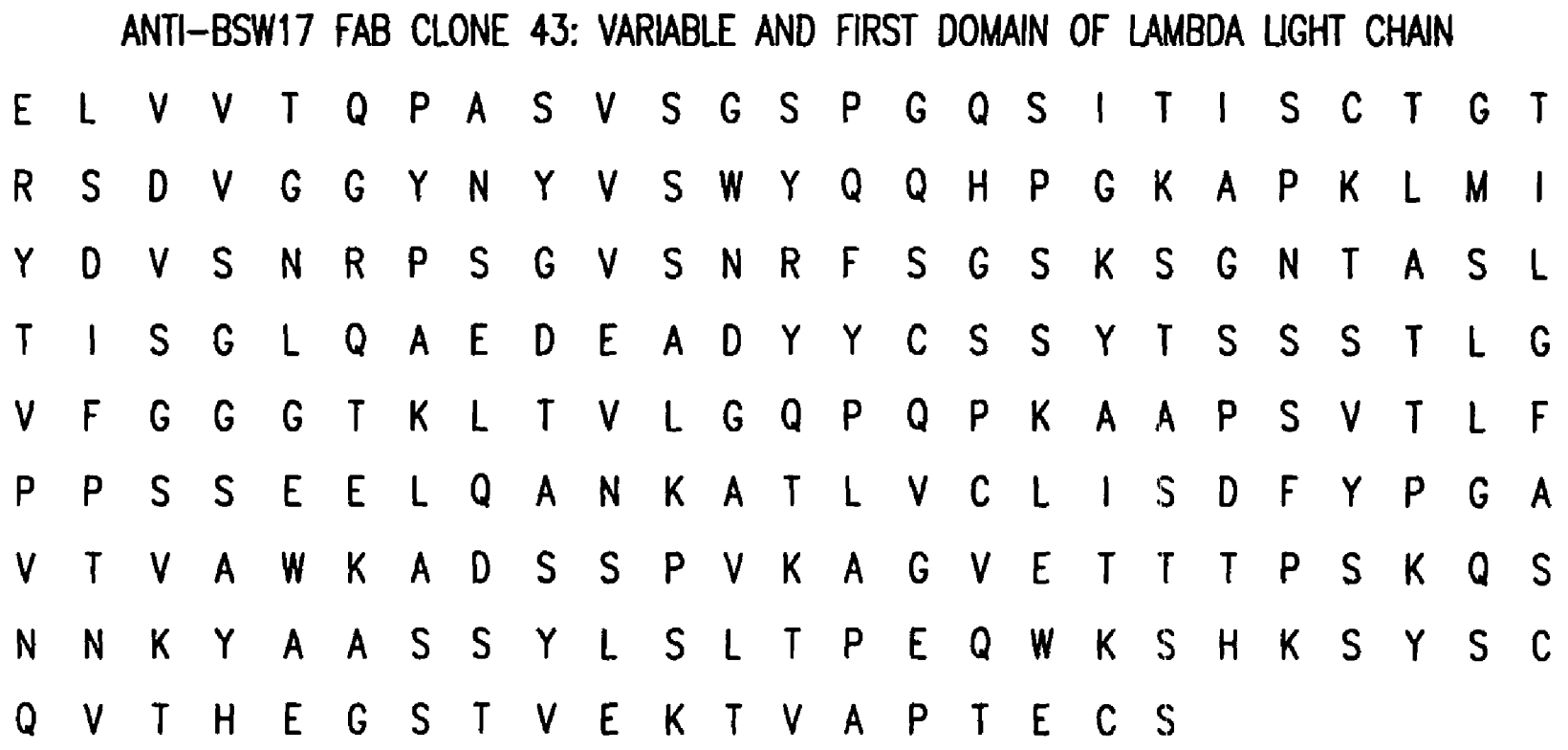

FIG. 12: Complete amino acid sequences for the heavy and light chain of the three recombinant BSW17-mimobodies:

FIG. 12a: Anti-id-BSW17, clone 52: variable and first constant domains of heavy chain (Seq.id. no. 35);

FIG. 12b: Anti-id-BSW17, clone 52: variable and constant domains of kappa light chain (Seq.id. no. 36);

FIG. 12c: Anti-id-BSW17, clone 43: variable and first constant domains of heavy chain (Seq.id. no. 37);

FIG. 12d: Anti-id-BSW17, clone 43: variable and constant domains of lambda light chain (Seq.id. no. 38).

Figure 4C:
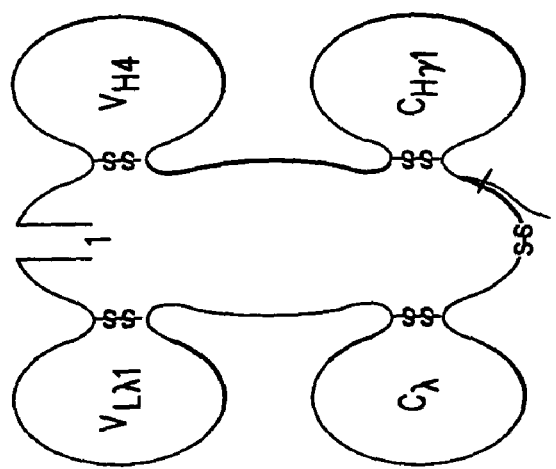
Figure 4B:
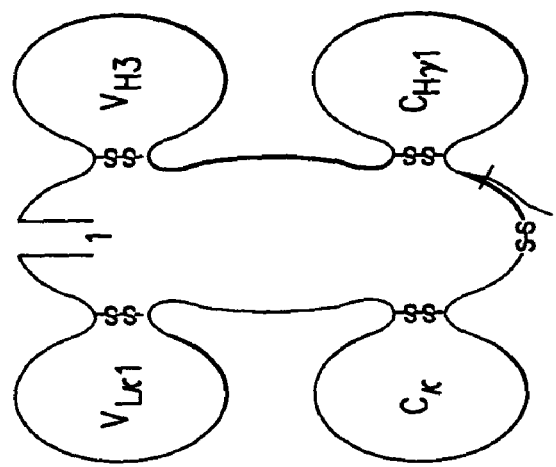
Figure 4A:
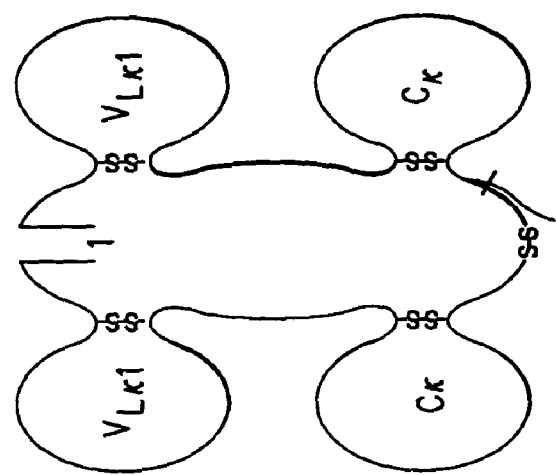

The mimobody $(L.C.)_2$ clone 52 comprises the light chains of FIG. 12b (Seq.id. no. 36) bound by disulfide bridges as indicated in FIG. 4A.

The mimobody Fab clone 52 comprises the light chain of FIG. 12b (Seq.id. no. 36) and the heavy chain of FIG. 12a (Seq.id. no. 35), bound by disulfide bridges as indicated in FIG. 4B.

The mimobody Fab clone 43 comprises the light chain of FIG. 12d (Seq.id. no. 38) and the heavy chain of FIG. 12c (Seq.id. no. 37), bound by disulfide bridges as indicated in FIG. 4C.

The following Examples illustrate the invention and are not limitative. Temperatures are in degrees Celsius. The following abbreviations are used:

anti-id=anti-idiotypic
ABTS=[2,2'-azinodi(3-ethyl-benzthiazoline) sulphonate]
BSA=bovine serum albumin
BSW17=mouse monoclonal anti-human IgE antibody; C$\epsilon$3 specific
CDR=complementarity determining regions
C$\epsilon$3=third heavy chain constant region domain of IgE
C$\epsilon$4=fourth heavy chain constant region domain of IgE
C$\epsilon$E=mimotope peptide mimicking the C$\epsilon$3 epitope region of BSW17
C$\epsilon$M=mimotope peptide mimicking the C$\epsilon$4 epitope region of BSW17
cfu=colony-forming units
ELISA=enzyme linked inmmunosorbent assay
Fab=antibody fragment lacking heavy chain constant regions 2 and 3
Fc$\epsilon$RI; IgERI=high affinity receptor for IgE
Fc$\epsilon$RI$\alpha$ =high affinity receptor for IgE, $\alpha$ chain
FCS=fetal calf serum
FR=framework regions
FITC=fluoresceine isothiocyanate-conjugated
HRP=horse radish peroxidase
HSA=human serum albumin
(h)IgE=(human) immunoglobulin E
mAb=monoclonal antibody
MNC=mononuclear cells
NIP=3-nitro4-hydroxy-iodophenyl acetic acid
p.c.=polyclonal
Phab=phage displaying Fab fragments (Fab expressing bacteriophage)
PBS=phosphate-buffered saline
PCA=passive cutaneous anaphylaxis
PWM=pokeweed mitogen
r=recombinant
RT=room temperature
SPR=surface plasmon resonance

EXAMPLE 1

Construction of Phage Display Libraries a) Source of Lymphocytes

Two male adult donors were used to prepare mononuclear cells (MNC) from peripheral blood. A first male adult atopic donor who had clinical symptoms of allergy was boosted with an intramuscular injection of 0.5 ml of alum-adsorbed tetanus toxoid (Te Anatoxal Bern, Swiss Serum and Vaccine Institute, Bern, Switzerland). The MNC were isolated 7 days later using Ficoll gradient centrifugation (Lymphoprep, Pharmacia, Milwaukee, Wis., USA) and then cultured for 3 days in RPMI-1640 medium (Seromed, Basel, Switzerland) containing $10^3$ U/ml of IL-2 (Sigma, St-Louis, Mo., USA), 50 μg/ml Pansorbin cells (Staphylococcus aureus Cowan strain1, Calbiochem, La Jolla, Calif., USA) and tetanus toxoid diluted at 1:1000 in RPMI-1640 medium. Total RNA was then prepared from these cells using a phenol-chloroform guanidium isothiocyanate procedure (Chomczynsi, P. and Sacci, N., *Anal. Biochem.* 162 [1987] 156). The second male adult donor, a hyperimmune Rhesus D donor, was given an i.v. boost of 2 ml of packed red blood cells from a known male donor of blood group 0 RhD+. The MNC were isolated by Ficoll gradient centrifugation at +18 days after the boost. The cells were first cultured for 3 days in RPMI-1640 medium containing $10^3$U/ml of IL-2 and 10 μg/ml of pokeweed mitogen (PWM; Sigma L9379, Buchs, Switzerland) before extracting RNA.

Human tonsil samples were obtained from three tonsillectomized children. Tonsils were macerated in RPMI-1640 medium in sterile petri dishes and cut into little pieces. Tissue, cells and medium were then transferred into sterile tubes, the tissue debris allowed to settle and MNC were isolated from the supernatant using Ficoll gradient centrifugation. B cells were selected by incubating the MNC with CD19-coated paramagnetic beads and then RNA was prepared according to the phenol-chloroform guanidium isothiocyanate procedure mentioned above.

The pComb3 vector used for cloning of the chains for all mimobodies was obtained from the Scripps Research Institute La Jolla, Calif., USA (Barbas III, C. F. and Lerner, R. A., *Companion Methods Enzymol.* 2 [1991] 119). The *Escherichia coli* strain XL1-Blue used for transformation of the pComb3 vector and the VCSM13 helper phage were purchased from Stratacyte (La Jolla, Calif., USA).

b) Construction of Bacteriophage Libraries

Three separate libraries were constructed: the first one called BS from the MNC isolated from the first male atopic donor, the second one called LD2 from the MNC harvested at +18 days after i.v. boost from the second male donor and the third one called CT from the B-cell enriched population of MNC isolated from the children's tonsils. Total RNA was prepared from these cells using the phenol chloroform guanidium isothiocyanate method. From this RNA, 10 μg were used to make cDNA using an oligo(dT) primer (400 ng) and reverse transcribed with M-MuLV reverse transcriptase according to the conditions specified by the supplier (Boehringer Mannheim, Germany). PCR amplification was performed as described in Vogel, M. et al., *E. J. of Immunol.* 24 (1994) 1200. Briefly, 100 μl of PCR reaction medium contained Perkin-Elmer buffer with 10 mM $MgCl_2$, 5 μl cDNA, 150 ng of each appropriate 5' and 3' primer, all four dNTP at 200 μM each and 2 U/ml Taq Polymerase (Perkin Elmer, N.J., USA). The PCR amplification of the heavy and light chains of the Fab molecule was performed separately with a set of primers from Stratacyte (details given below). For the heavy chain six upstream primers were used that hybridize to each of the six families of the $V_H$ genes, whereas one kappa and one lambda chain primer were used for the light chains. The downstream primers were designed to match the hinge region of the constant domains γ1 and γ3 for the heavy chain. For the light chain the downstream primers were matched to the 3' end of kappa and lambda constant domains. The heavy and light chain PCR products were pooled separately, gel-purified and cut with Xho1/Spe1 and Sac1/Xba1 restriction enzymes (Boehringer Mannheim, Germany), respectively. After digestion the PCR products were extracted once with phenol: chloroform: isoamyl alcohol and purified by gel excision. The insertion of the Xho1/Spe1 digested Fd fragment and subsequent ligation of the Sac1/Xba1 digested light chain into the pComb3 vector, the transformation into XL1-Blue cells, and the production of phages were performed as described in Barbas III, C. F. and Lerner, R. A., *Companion Methods Enzymol.* 2[1991] 119. After transformation of the XL1-Blue *E.coli* cells samples were withdrawn and titrated on plates to determine the library size. These results indicated expression libraries of $1\times10^7$, $7.7\times10^6$ and $3\times10^6$ cfu (colony forming units) for BS, LD2 and CT respectively.

c) PCR Primers containing $2\times10^{12}$ cfu of each phage library (BS, LD2 and CT). The phages were then transferred into the second tube and the process was repeated once. After the second pre-absorption the non-Le27-specific phages were added to a tube coated with 4 ml of BSW17 (20 μg/ml) and blocked with PBS/2% skimmed milk as described above. After incubation for 2 h at RT on a under-and-over-turntable the tube was washed successively 10 times with PBS/0.1% Tween and 10 times with PBS. The adherent phages were eluted successively with, first, 500 μl of 0.1 M triethylamine and then after three times rinse in PBS, with 500 μl of 0.1 M HCl adjusted to pH 2.2 with glycine and containing 1 mg/ml BSA. Each elution step was carried out for 10 min at RT and the eluted phages were neutralized with 250 μl of 1 M Tris.Cl, pH 7.4 and 30 μl of 2 M Tris base, respectively. The selected phages were amplified using *E. coli* XL1-Blue cells as described in Barbas and Lerner, supra (1991) before being subsequently used in three more rounds of panning. After each round of panning the titer of eluted phages was monitored by cfu determination (Table 2):

TABLE 2

Enrichment of BSW17 specific Phabs by consecutive rounds of panning

| Round of panning[a] | Number of eluted phages (cfu) |
|---|---|
| 1 | $3 \times 10^5$ |
| 2 | $2 \times 10^4$ |
| 3 | $3 \times 10^5$ |
| 4 | $5 \times 10^7$ |

[a] For each round of panning $6 \times 10^{12}$ phage particles were preabsorbed twice in tubes coated with 20 μg/ml of Le27 followed by incubation in one tube coated with 20 μg/ml of BSW17

| | | |
|---|---|---|
| VHI | 5'-CAC TCC CAG GTG CAG CTG CTC GAG TCT GG-3' | (Seq.id.no. 9); |
| VHII | 5'-GTC CTG TCC CAG GTC AAC TTA CTC GAG TCT GG-3' | (Seq.id.no. 10); |
| VHIII | 5'-GTC CAG GTG GAG GTG CAG CTG CTC GAG TCT GG-3' | (Seq.id.no. 11); |
| VHIV | 5'-GTC CTG TCC CAG GTG CAG CTG CTC GAG TCG GG-3' | (Seq.id.no. 12); |
| VHV | 5'-GTC TGT GCC GAG GTG CAG CTG CTC GAG TCT GG-3' | (Seq.id.no. 13); |
| VHVI | 5'-GTC CTG TCA CAG GTA CAG CTG CTC GAG TCA GG-3' | (Seq.id.no. 14); |
| CHI(γI) | 5'-AGC ATC ACT AGT ACA AGA TTT GGG CTC-3' | (Seq.id.no. 15); |
| VL(κ) | 5'- GT GCC AGA TGT GAG CTC GTG ATG ACC CAG TCT CCA-3' | (Seq.id.no. 16); |
| CL(κ) | 5'- T CCT TCT AGA TTA CTA ACA CTC TCC CCT GTT GAA GCT CTT TGT GAC GGG CGA ACT C-3' | (Seq.id.no. 17); |
| VL(λ) | 5'- C TGC ACA GGG TCC TGG GCC GAG CTC GTG GTG ACT CA-3' | (Seq.id.no. 18); |
| CL(λ) | 5'- G CAT TCT AGA CTA TTA TGA ACA TTC TGT AGG GGC-3' | (Seq.id.no. 19). |

EXAMPLE 2

Selection of Recombinant BSW17-specific Antibody Fragments (BSW-17-mimobodies) from Phase Libraries Selection of BSW17-specific phages was carried out by performing four rounds of panning. Each round comprised two pre-absorptions on the anti-IgE mAb Le27 before absorption on the anti-IgE mAb BSW17. Preabsorption was performed as follows: two immunotubes (Maxisorp, Nunc) were coated with 4 ml of Le27 (20 μg/ml) overnight at 4°, then blocked for 2 h at 37° with 4 ml of PBS/2% skimmed milk. A first tube was incubated on a under-and-over turn-table at RT for 30 min with 4 ml of blocking solution

EXAMPLE 3

Nucleotide Sequence of Recombinant BSW17-mimobodies

Plasmid DNA from selected phage clones was prepared using a Nucleotrap kit (Machery-Nagel, Düren, Germany) and nucleic acid sequencing was carried out on an ABI 373A sequencing system using a PRISM Ready Reactin DyeDeoxy Terminator Cycle Sequencing Kit (Applied Biosystems, Germany).

Primers used for sequencing of the heavy chain sequence were:

CHγ1   (5'-CGCTGTGCCCCCAGAGGT-3')      (Seq.id.no. 20) and pCH    (5'-GGCCGCAAATTCTATTTCAAGG-3')  (Seq.id.no. 21).

To obtain the light chain sequences the following primers were used:

Cλ    (5'-GAGACACACCAGTGTGGC-3')  (Seq.id.no. 22),

Cκ    (5'-CACAACAGAGGCAGTTCC-3')  (Seq.id.no. 23) and pCL   (5'-CTAAACTAGCTAGTCGCC-3')  (Seq.id.no. 24).

The primers were synthesized by Microsynth (Balgach, Switzerland). From the DNA sequences of a selection of various phage clones, two different amino acid sequences for BSW17-specific, recombinant antibody heavy and light chains were deduced (clone 52, clone 43). The sequences and their allocation to hypervariable regions (CDR) and framework sequences are shown in FIGS. 5a to 5d (Seq.id.no. 1 to 8).

Alignment of the amino acid sequences of the BSW17-specific recombinant antibody fragments displayed by clones 52 and 43 with human IgE reveals homologies with stretches of the human Cε3 domain which is involved in binding to the high affinity receptor (FIG. 6) (Seq.id.no. 25 to 34). Thus, the paratopes displayed by the recombinant antibody fragments mimic defined structures present in human IgE ("mimobodies"). Antibodies generated in allergic patients by vaccination with these recombinant mimobodies will therefore recognize human IgE and prevent allergic reactions by inhibiting IgE/IgERI binding.

EXAMPLE 4

Preparation and Purification of Recombinant BSW17-mimobodies

Soluble mimobodies derived from phage clones 43 and 52 (FIG. 5) (Seq.id.no. 1 to 8) were generated. In order to produce soluble Fab fragments the sequence gIII encoding the pIII tail protein of the phage particle was removed and replaced by a hexahistidine tag to facilitate the purification of the Fab fragment by $Ni^{2+}$-chelate affinity chromatography.

Phagemid DNA was prepared using a Nucleotrap kit (Macherey-Nagel, Düren, Germany) and digested with SpeI and NheI. The 4.7 kb DNA fragment lacking the gIII portion was treated with alkaline phosphatase and purified by agarose gel electrophoresis. The linearized DNA was ligated with a six histidine encoding DNA fragment at the 5' and 3' ends of SpeI and NheI restriction sites, respectively. After ligation the DNA was transformed into *E. coli* XL1-Blue cells and individual clones producing soluble mimobodies were selected. One of these clones was chosen for large scale purification and was grown in 1 l SB (Super Broth) containing 50 μg/ml carbenicillin at 37° to an OD of 1.0 at 600 nm. Culture was then induced with 1 mM isopropyl β-D-thiogalactopyranoside (IPTG) (Biofinex, Praroman, Switzerland) and grown for 4 h at 37°. Bacteria were pelleted at 6000 rpm for 20 min at 4°, resuspended in 30 ml sonication buffer (0.1 M NaPO4, 8 M urea, pH 8.0) and subsequently sonicated on ice. Insoluble components were then removed by centriflugation at 15'000 rpm for 30 min at 4° and the supernatant containing Fab was purified on a 1 ml of nickel-nitriloacetate column. The column was washed with sonication buffer to remove contaminants followed by two elution steps with sonication buffer at pH 5.1 and 4.9, respectively. Fractions were monitored at OD 280 nm and aliquots were analysed by SDS-PAGE (12% non reducing) to confirm mimobody purity and identity. Fractions containing mimobodies were then pooled, concentrated and dialysed against PBS.

The purity of the final mimobody preparations (as specified in FIGS. 4 and 12) (Seq.id. no. 35, 36, 37, 38) was evaluated by assaying a sample by SDS-PAGE. Protein bands were detected by Coomassie blue staining. The concentration was determined by comparing the Coomassie blue stained mimobody band with known amounts of a standard protein (BSA) and also by spectrophotometry. These mimobody preparations were subsequently used for competitive binding assay and for immunization of rabbits.

EXAMPLE 5

Inhibition of BSW17-mediated Displacement of Receptor-bound IgE by Recombinant BSW17-mimobodies BSW17 recognizes and displaces IgE bound to its high affinity receptor. In order to determine that the anti-id BSW17 rFab fragments are able to inhibit this displacement reaction, a competitive binding assay using IgE attached to cell surface exposed IgERI was performed. A recombinant chinese hamster ovary cell line (CHO), stably transfected with DNA encoding the α-chain of human IgERI was used for the assay [CHOα cell line; Blank, U. et al., *Eur.J.Biol.Chem.* 266 (1991) 2639]. A series of test samples containing $5\times10^4$ CHOα cells were incubated in FACS buffer (PBS, 0.3% BSA, 0.02% $NaN_3$) with 48 ng of IgE B11 hybridoma (Zürcher, A. W. et al., *Immunol.Lett.* 46 (1995) 49–57] for 15 min at RT. After washing once with FACS buffer each sample was incubated for 15 min at RT with preformed complexes of fluoresceine isothiocyanate-conjugated BSW17 (BSW17-FITC) and increasing amounts of anti-id BSW17 rFabs. The complexes were prepared as follows: 50 μl of BSW17-FITC at a concentration of 1.3 mM were incubated with different amounts of anti-id-BSW17 rFabs (40 nM; 200 nM; 1 μM; 4 μM; and 40 μM) for 30 min at RT. A control sample containing only the CHOα cells was incubated for 15 min at RT with BSW17-FITC for determination of non-specific binding. The CHOα cells were washed once with FACS buffer and after addition of 100 μl of FACS buffer the cells were analysed in a FACSCalibur (Becton Dickinson) flow cytometer equipped with an Argon laser tuned to 488 nm. Gates in the forward scatter/side scatter dot blot were set around monomeric cells and fluorescence was quantitated and expressed as mean channel fluorescence (mcf). The percentage of positive cells was calculated as the percentage of BSW17 binding to CHOα cells. As seen in FIG. 7, the binding of BSW17 to CHOα cells decreased with increasing concentrations of anti-id-BSW17 Fab fragments, indicating that the two anti-id BSW17 Fab clones were able to inhibit the binding of BSW17 to IgE.

EXAMPLE 6

Immunization of Rabbits with Recombinant BSW17 Mimobodies

This Example shows that immunization with either anti-BSW17 rFab (consisting of heavy plus light chain of clone 52 as shown in FIG. 4B together with FIGS. 12a and 12b) (Seq.id.no. 35 and 36), or the recombinant mimobody consisting of only the light chain (FIG. 4A together with FIG. 12b) (Seq.id.no. 36) induces in rabbits a humoral immune response which crossreacts with human IgE. Two New Zealand white female rabbits were given a primary immunization subcutaneously with 300 µg/ml anti-BSW17 rFab or light chain fragment of clone 52, emulsified 1:1 in Freund's complete adjuvant and then boosted three times with the same amount of mimobody emulsified 1:1 in Freund's incomplete adjuvant every two weeks. Sera were collected at day 0 (pre-bleed) and animals were bled 7 days after the last injection.

Rabbit immune sera were purified by immunoaffinity chromatography using human IgE (SUS-11 IgE), chemically crosslinked to Sepharose 4B columns. By this procedure the anti-hIgE fraction can be isolated from total immunoglobulins allowing accurate characterization of the therapeutically relevant immune response with respect to antibody titers and affinity.

The immunoaffinity purification of anti-mimobody antibodies which crossreact with human IgE consisted of two steps. In the first step the IgG fraction was isolated from the rabbit antiserum by ammonium sulfate precipitation, in the second step the hIgE-specific anti-BSW17 mimobody antibodies were bound to human IgE (SUS-11 IgE), covalently coupled to CH-Sepharose 4B, followed by elution, dialysis and concentration.

Concentration-dependent complex formation of the immunoaffinity-purified immunoglobulins with human IgE in solution was confirmed by ELISA: SUS-11 IgE was incubated with equimolar amounts of anti-mimobody immunoglobulins overnight at 4°. The complexes formed in solution were added to microtiter plate wells which had been coated with the monoclonal anti-hIgE antibody LE27 as capturing antibody. Bound anti-mimobody IgG was detected with polyclonal anti-rabbit IgG-HRP. The results are shown in FIG. 8.

EXAMPLE 7

Immunization of Mice with Recombinant BSW17 Mimobodies

Recombinant mimobodies derived from both clone 43 and clone 52 can induce anti-mimobody antibodies. Immunizations were carried out in mice. Groups of five Balb/c mice were injected subcutaneously with 5 µg per mouse of recombinant BSW17 mimobodies which had been produced in *E. coli* bacteria and purified by nickel affinity chromatography.

Aluminum hydroxide was used as adjuvant:
  Group 1 was immunized with batch SDS426=anti-Id-BSW17.52; light chain
  Group 2 was immunized with batch SDS427=anti-id-BSW17.52; Fab
  Group 3 was immunized with batch SDS463=anti-Id-BSW17.43; Fab On days 21 and 41 after primary immunization, two booster injections (5 µg per mouse) were administered. Blood samples were taken on days 0, 20, 28, 35, 42, 49 and 56 after primary immunization. Serum was prepared and probed for the presence of anti-mimobody antibodies by ELISA.

Microtiter plate wells were coated with 1 µg/ml polyclonal human IgG and incubated with 1:50 diluted mouse sera prepared from blood samples taken at the indicated time points after primary immunization. Bound anti-mimobody antibodies (ahIgG, directed against the human framework and constant domain regions) were detected by a second incubation with horse radish peroxidase conjugated goat anti-mouse IgG (gamIgG-HRP). The colour reaction was developed using chromogenic ABTS substrate.

All mice produced anti-mimobody antibodies after the second boost with all recombinant mimobody preparations (FIG. 9).

EXAMPLE 8

Immunoglobulins Generated in Rabbits Against Recombinant BSW17 Mimobodies Bind to Human IgE with High Affinity Vaccination with recombinant BSW17 mimobodies is shown here to induce a humoral immune response with high affinity for human IgE. The kinetic parameters representative for the binding of the immunoaffinity-purified anti-mimobody immunoglobulins to human IgE were analyzed by surface plasmon resonance (SPR).

SPR measurements were performed in a BIAcore instrument (Biacore, Uppsala, Sweden). Specific binding surfaces were prepared by coupling human IgE or murine IgG$_3$ to a CM5 sensor chip using amine coupling according to the manufacturer's instructions. Using this procedure, biomolecules are attached via primary amino groups to the carboxymethylated dextran surface of the sensor chip. 10 pmoles of human myeloma IgE or SUS-11 IgE were coupled to separate flow cells of the chip. The murine IgG$_3$ mAb, ABL 364 (ATCC HB 9324), was immobilized to a separate track of the same sensor chip. ABL 364 was used as a reference for determining binding of the anti-mimobody antibodies to non-hIgE immunoglobulin structures and to correct for possible changes of the refractive index caused by buffer changes.

Coupling densities were~13000 RU.

All biomolecular interactions measured in the BIAcore instrument were carried out at 25°, using HBS (10 mM Hepes, pH=7.4, 150 mM NaCl, 3.4 mM EDTA, and 0.005% v/v surfactant P-20) as the continuous flow buffer. The concentration range of each analyte passed over the sensor chip surface for kinetic analysis was from 33 nM to 499 nM. The flow rate was 5 µl/min. The analytes were injected for 1200 s, followed by HBS for approximately 1800 s to monitor the dissociation of bound analyte. The chip was regenerated with a 120 s pulse of 10 mM HCl. Non-specific binding was monitored by passing the analytes over the ABL 364 control track to be subtracted from specific binding prior to kinetic analysis.

Binding curves generated by SPR measurements were analyzed using the BIAevaluation 3.0 analysis package. For relative comparison of the anti-mimobody/IgE interactions a monophasic model was used. Association rate konstants $k_a$, dissociation rate constants $k_d$ and the equilibrium dissociation constants $K_D=1/K_A$ ($K_A$ =affinity constant) were calculated for every curve and are summarized in Table 3:

TABLE 3

Kinetic constants (SPR/BIAcore) of the interaction between polyclonal (p.c.) rabbit anti-mimobody Ig preparations and hIgE

|  |  | Myeloma IgE | SUS-11 IgE |
| --- | --- | --- | --- |
| BSW17 | $K_a$ (1/Ms) | n.d. | $0.8 \pm 0.3 \times 10^4$ |
|  | $K_d$ (1/s) | n.d. | $4.2 \pm 0.9 \times 10^{-6}$ |
|  | $K_D$ (nM) | n.d. | $0.53 \pm 0.33$ |
| a(anti-id-BSW17.52; light chain)[1] | $K_a$ (1/Ms) | $2.1 \pm 0.8 \times 10^4$ | $2.2 \pm 0.9 \times 10^4$ |
| (SDS410) | $K_d$ (1/s) | $2.8 \pm 0.5 \times 10^{-4}$ | $2.3 \pm 0.2 \times 10^{-4}$ |
|  | $K_D$ (nM) | $13.3 \pm 6.8$ | $10.7 \pm 3.3$ |
| a(anti-id-BSW17.52; Fab)[2] | $K_a$ (1/Ms) | $4.6 \pm 2.7 \times 10^4$ | $2.5 \pm 1.0 \times 10^4$ |
| (SDS 411) | $K_d$ (1/s) | $2.3 \pm 0.3 \times 10^{-4}$ | $1.5 \pm 0.1 \times 10^{-4}$ |
|  | $K_D$ (nM) | $5.0 \pm 2.2$ | $6.0 \pm 1.8$ |
| a(anti-id-BSW17.43; Fab)[3] | $K_a$ (1/Ms) | u.d. | $2.2 \pm 0.4 \times 10^4$ |
| (SDS476) | $K_d$ (1/s) | u.d. | $1.6 \pm 0.1 \times 10^{-5}$ |
|  | $K_D$ (nM) | u.d. | $0.75 \pm 0.02$ | a = anti-
n.d. = not determined
[1] i.e. anti-SDS426
[2] i.e. anti-SDS427
[3] i.e. anti-SDS463

It appears that high affinity antibodies against human IgE could be induced in rabbits immunized with recombinant BSW17-mimobodies ($K_D$ values in nanomolar range). Clone 43-derived Fab (SDS463; FIG. 4C; anti-id-BSW17.43) has the capacity to induce an immune response of very high affinity for human IgE ($K_D$<1 nM).

Thus by using a monoclonal anti-idiotypic antibody it was possible to induce a strong polyclonal response against IgE as intended by the human vaccination strategy.

EXAMPLE 9

Immunoglobulins Generated in Rabbits Against Recombinant BSW17-mimobodies Inhibit Binding of Human IgE to its High Affinity Receptor For being active as an anti-allergy vaccine, complex formation between anti-mimobody antibodies and hIgE is expected to prevent IgE from binding to its high affinity receptor. The Cε3 epitope region Val(370)-Gly(379) in stretch Val(370-Asn(383) (FIG. 6) (Seq.id.no. 25) which shows amino acid sequence homology with BSW17-mimobody CDR is involved in high affinity receptor binding. Therefore, IgE-specific antibodies raised against the recombinant BSW17 mimobodies are expected to exert their therapeutic effect by inhibiting binding of IgE to its high affinity receptor by blocking the binding domain. To confirm this, the purified anti-mimobody antibodies obtained from immunized rabbits were tested for inhibition of hIgE/FcεRIα binding in a competition ELISA. As a disease-relevant readout, free IgE was measured by its ability to bind to recombinant FcεRIα (RIα-HSA-RIα double fusion protein; DFP) (FIG. 10).

hIgE (SUS-11; 1 µg/ml in FIG. 10A and 0.1 µg/ml in FIG. 10B) was pre-incubated 16 hrs at +4° with increasing amounts of anti-mimobody immunoglobulins or mAb BSW17 as a reference. The bulk immunoglobulins present in the immunoaffinity column flowthrough of the SDS410 preparation was included as a negative control. The formed complexes were added to microtiter plate wells coated with 1 g/ml of the anti-IgE antibody Le27 as a catching antibody and incubated with horse radish peroxidase labeled FcεRIα-HSA -FcεRIα double fusion protein (DFP) for 1 hr at 37°. Bound DFP was detected with a chromogenic substrate. O.D. values are expressed as % binding. Binding to competitor-free SUS-11 IgE was set as 100%. Mean values of measurements made in duplicate are shown. Variations were generally below 2%.

The results show that immunization with BSW17 mimobodies results in the generation of specific high affinity anti-hIgE antibodies in rodents. These anti-mimobody antibodies inhibit the binding of IgE to its high affinity receptor in vitro, indicating the value of the BSW17-mimobody vaccination strategy for anti-allergy vaccine development.

EXAMPLE 10

Inhibition of Passive Cutaneous Anaphylaxis by Vaccination of Rhesus Monkeys with Recombinant BSW17 Mimobodies Inhibition of passive cutaneous anaphylaxis (PCA) in monkeys can be used to test the anti-allergic activity of compounds in vivo.

Mimobody vaccination results in inhibition of anaphylactic skin reactions in rhesus monkeys. Groups of two monkeys were injected subcutaneously with 500 µg per animal of recombinant anti-BSW17 mimobodies. After primary immunization, two booster injections were administered. About 10 days after each boosting, PCA tests were performed. Monkeys VI 91, VI 92, VI 93 and VI 95 were tested for PCA reaction once more three months after the last boosting injection. The immunization scheme is summarized in the following Table 1:

TABLE 1

| Monkey | Immunogen | Boosting (day no.) | PCA (day no.) |
|---|---|---|---|
| VI 91 | anti-id-BSW17.52; light chain (SDS426) (FIG. 4A) | 0, 21, 54, 92 | 0, 30, 61, 105, 203 |
| VI 92 | anti-id-BSW17.52; light chain (SDS426) (FIG. 4A) | 0, 21, 54, 92 | 0, 30, 61, 105, 203 |
| VI 93 | anti-id-BSW17.52; Fab (SDS427) (FIG. 4B) | 0, 21, 54, 92 | 0, 30, 61, 105, 203 |
| VI 95 | anti-id-BSW17.52; Fab (SDS427) (FIG. 4B) | 0, 21, 54, 92 | 0, 30, 61, 105, 203 |
| VI 2 | anti-id-BSW17.43; Fab (SDS463) (FIG. 4C) | 0, 21, 54, 112 | 0, 33, 64, 123 |
| VI 75 | anti-id-BSW17.43; Fab (SDS463) (FIG. 4C) | 0, 21, 54, 112 | 0, 33, 64, 123 |

Rhesus monkeys pretreated with small doses of ketamine hydrochloride (10–15 mg/kg, i.m.) (Ketalar®, Parke Davis, GB) to keep them immobilized, received i.c. injections of various doses of IgE (3W8) (Serotec, Oxford, U.K.) into the skin of the abdomen. IgE (JW8) is a chimaeric antibody consisting of a mouse antigen-binding part specific for the hapten NIP and a human Fcε heavy chain. Increasing amounts (0, 2, 10, 50, 250 ng/ml saline) of IgE (JW8) were injected in a cephalocaudal series with a 30 gauge needle in a volume of 100 μL. Two hours later, 25 mg of NIP conjugated to BSA were administered i.v. per animal. The animals were sedated again after the intravenous challenge with NIP-BSA conjugate. For the visualization of the skin reaction, Evans blue dye (1%, 0.5 ml/kg) was injected intravenously immediately after the antigen challenge. The skin reactions were read 20 min after antigen injection by measuring two diameters of the blue spot and calculating their mean in mm.

PCA was tested at the indicated time points after primary immunization and boosting. PCA intensity was calculated from the area under the curves (AUC) generated by meters of the blue skin areas against the injected IgE (JW8) concentrations. The PCA scores shown in Table 4 for each single monkey represent the calculated AUC values:

TABLE 4

Effect of BSW17-mimobody vaccination on passive cutaneous anaphylaxis in rhesus monkeys

A

| | PCA score | | | |
|---|---|---|---|---|
| | Immunogen: anti-id-BSW17.52; light chain (SDS426) (FIG. 4A) | | Immunogen: anti-id-BSW17.52; Fab (SDS427) (FIG. 4B) | |
| Days after immunization | Monkey VI91 | Monkey VI92 | Monkey VI93 | Monkey VI95 |
| 0 | 11.6[1] (100)[2] | 10.6 (100) | 15.8 (100) | 15.6 (100) |
| 30 | 10.5 (91) | 10.5 (99) | 15.4 (97) | 16.8 (108) |
| 61 | 10.1 (87) | 1.8 (17) | 21.4 (139) | 16.5 (106) |
| 105 | 4.6 (40) | 2.1 (20) | 5.6 (35) | 7.0 (45) |
| 203 | 9.8 (84) | 6.3 (59) | 12.6 (80) | 11.2 (72) |

B

| | PCA score Immunogen: anti-id-BSW17.43; Fab (SDS463) (FIG. 4C) | |
|---|---|---|
| Days after immunization | Monkey VI2 | Monkey VI75 |
| 0 | 15.8[1] (100)[2] | 15.8 (100) |
| 33 | 16.5 (104) | 18.9 (120) |
| 64 | 9.8 (62) | 13.0 (82) |
| 124 | 16.8 (106) | 18.9 (120) |

[1] PCA scores calculated from the area under the curves (AUC) generated by plotting the diameters of the blue skin areas against the injected IgE (JW8) concentrations as previously described (77)
[2] PCA intensity relative to pre-immunization values. PCA at day 0 = 100%

Taking the individual pre-immunization PCA scores (day 0 values) as a reference, all monkeys responded to BSW17 mimobody vaccination with a reduction of PCA intensity. Best results were obtained with the clone 52 light chain construct (SDS426) (FIG. 4A) with inhibition rates of 60–83% (PCA scores 40 and 17). Monkeys immunized with clone 52 Fab (batch SDS427) (FIG. 4B) suppressed PCA by 55–65% (PCA scores 45 and 35). A somewhat lower PCA inhibition ranging from 18–38% (PCA scores 82 and 62) was observed with clone 43 Fab (batch SDS463) (FIG. 4C), despite its superiority over clone 52 mimobodies with respect to BSW17 binding and high affinity anti-hIgE induction in rabbits.

Following on the vaccination protocol, vaccination with clone 52 mimobodies became effective after the third boosting injection (except monkey VI92) and partial PCA suppression was still observed more than 3 months later. In contrast, clone 43 Fab was effective after the second boosting injection, whereas a third mimobody challenge had no effect.

The average PCA score profile for each group of two monkeys immunized with the same mimobody preparation, calculated from the single monkey values of Table 4, is shown in FIG. 11.

A positive PCA result in vaccinated monkeys (relative to individual pre-treatment scores or untreated control animals) is a clear indication for the efficacy of mimobody vaccination and proves the validity of its mechanistic concept. Vaccination of rhesus monkeys with recombinant BSW17 mimobodies results in the generation of high affinity anti-human IgE antibodies which inhibit PCA in vivo.

What is claimed is:

1. A composition comprising a member selected from the group consisting of an antibody and an isolated antibody fragment that is anti-idiotypic to the monoclonal antibody produced by the hybridoma cell line deposited with the ECACC under accession number 96121916, wherein said antibody or antibody fragment comprises complementarity determining regions which comprise a first polypeptide comprising the amino acid sequence set out in SEQ ID NO:2 and a second polypeptide comprising the amino acid sequence set out in SEQ ID NO:4.

2. A composition comprising a member selected from the group consisting of an antibody and an isolated antibody fragment that is anti-idiotypic to the monoclonal antibody produced by the hybridoma cell line deposited with the ECACC under accession number 96121916, wherein said antibody or antibody fragment comprises complementarity determining regions which comprise two polypeptides each of which comprises the amino acid sequence set out in SEQ ID NO:4.

3. A composition comprising a member selected from the group consisting of an antibody and an isolated antibody fragment that is anti-idiotypic to the monoclonal antibody produced by the hybridoma cell line deposited with the ECACC under accession number 96121916, wherein said antibody or antibody fragment comprises complementarity determining regions which comprise a first polypeptide comprising the amino acid sequence set out in SEQ ID NO:6 and a second polypeptide comprising the amino acid sequence set out in SEQ ID NO:8.

4. A composition comprising a member selected from the group consisting of an antibody and an isolated antibody fragment that is anti-idiotypic to the monoclonal antibody oroduced by the hybridoma cell line deposited with the ECACC under accession number 96121916, wherein said antibody or antibody fragment comprises complementarity determining regions consisting of the amino acid sequences set forth in SEQ ID NO:52, SEQ ID NO:54, SEQ ID NO:56, SEQ ID NO:58, SEQ ID NO:60, and SEQ ID NO:62.

* * * * *